US009823534B2

(12) United States Patent
Aiken et al.

(10) Patent No.: US 9,823,534 B2
(45) Date of Patent: Nov. 21, 2017

(54) ELECTROCHROMIC SINGLE AND TWO-CORE VIOLOGENS AND OPTICAL ARTICLES CONTAINING THEM

(71) Applicant: ESSILOR INTERNATIONAL (COMPAGNIE GENERALE D'OPTIQUE), Charenton-le-Pont (FR)

(72) Inventors: Stuart Aiken, York (GB); Christopher David Gabbutt, Preston (GB); Bernard Mark Heron, Brough (GB); Claudine Biver, Charenton-le-Pont (FR); Samuel Archambeau, Charenton-le-Pont (FR); Fabien Berit-Debat, Charenton-le-Pont (FR); Sandrine Duluard, Toulouse (FR)

(73) Assignee: ESSILOR INTERNATIONAL (COMPAGNIE GENERALE D'OPTIQUE), Charenton-le-Pont (FR)

( * ) Notice: Subject to any disclaimer, the term of this patent is extended or adjusted under 35 U.S.C. 154(b) by 62 days.

(21) Appl. No.: 15/022,784

(22) PCT Filed: Sep. 16, 2014

(86) PCT No.: PCT/EP2014/069737
§ 371 (c)(1),
(2) Date: Mar. 17, 2016

(87) PCT Pub. No.: WO2015/040033
PCT Pub. Date: Mar. 26, 2015

(65) Prior Publication Data
US 2016/0231635 A1 Aug. 11, 2016

(30) Foreign Application Priority Data
Sep. 17, 2013 (EP) .................................. 13184771

(51) Int. Cl.
*G02F 1/153* (2006.01)
*G02F 1/15* (2006.01)
*C09K 9/02* (2006.01)
*C07D 213/22* (2006.01)
*C07D 403/06* (2006.01)
*G02C 7/10* (2006.01)

(52) U.S. Cl.
CPC ......... *G02F 1/1521* (2013.01); *C07D 213/22* (2013.01); *C07D 403/06* (2013.01); *C09K 9/02* (2013.01); *G02C 7/101* (2013.01); *C09K 2211/1007* (2013.01); *C09K 2211/1011* (2013.01); *C09K 2211/1029* (2013.01); *G02F 2001/151* (2013.01); *G02F 2001/1517* (2013.01)

(58) Field of Classification Search
CPC .................................................... G02F 1/1521
USPC ........................................................ 359/275
See application file for complete search history.

(56) References Cited

U.S. PATENT DOCUMENTS

| 4,116,535 A | 9/1978 | Ponjee et al. ................. 359/272 |
| 5,278,693 A | 1/1994 | Theiste et al. ................. 359/272 |
| 5,438,024 A | 8/1995 | Bolton et al. ................... 501/55 |
| 5,998,617 A | 12/1999 | Srinivasa et al. ............. 544/347 |
| 6,141,137 A | 10/2000 | Byker et al. ................... 359/265 |
| 6,255,238 B1 | 7/2001 | Brocheton ...................... 501/56 |
| 7,106,489 B2 | 9/2006 | Berneth et al. ................ 359/273 |
| 8,736,946 B2 | 5/2014 | Archambeau et al. ........ 359/275 |
| 2002/0027700 A1 | 3/2002 | Berneth et al. ................ 359/265 |
| 2005/0231784 A1* | 10/2005 | Shinohara .............. B82Y 20/00 359/265 |
| 2009/0082570 A1 | 3/2009 | Nii et al. ....................... 546/258 |
| 2011/0235150 A1 | 9/2011 | Das et al. ...................... 539/273 |

FOREIGN PATENT DOCUMENTS

| EP | 0180204 | 5/1986 |
| EP | 1156098 | 11/2001 |
| EP | 2407526 | 1/2012 |
| EP | 2848667 | 3/2015 |
| EP | 2848668 | 3/2015 |
| FR | 2937154 | 4/2010 |
| FR | 2950710 | 4/2011 |
| GB | 1514466 | 6/1978 |
| JP | S52135884 | 11/1977 |
| JP | S5437080 A | 3/1979 |
| JP | H11106376 | 4/1999 |
| WO | WO 98/44384 | 10/1998 |
| WO | WO 2006/013250 | 2/2006 |
| WO | WO 2008/028930 | 3/2008 |
| WO | WO 2010/024840 | 3/2010 |
| WO | WO 2011/082354 | 7/2011 |

(Continued)

OTHER PUBLICATIONS

Database CA [Online] Chemical Abstracts Service, Columbus, Ohio, US; 1982 "Composition for electrochromic displays", XP002724222, retrieved from STN Database accession No. 1982:605815 abstract-& JP 57 057779 A (Mitsubishi Electric Corp., Japan) Apr. 7, 1982 (Apr. 7, 1982).
Database CA [Online] Chemical Abstracts Service, Columbus, Ohio, US; 1980, "Electrochromic substances for display devices", XP002724143, retrieved from STN Database accession No. 1980:613419 abstract- & JP 55 054381 A (Hitachi, Ltd., Japan) Apr. 21, 1980 (Apr. 21, 1980).
Clennan et al., "Pyrylogens: Synthesis, Structural, Electrochemical, and Photophysical Characterization of a New Class of Electron Transfer Sensitizers", *J Am Chem Soc*, 130(24): 7552-3, 2008.
Downes, "Aryl-substituted Derivatives of 4,4'-Bipyridylium Salts: their Spectroscopic Properties and Stereochemistry", *J. Chem. Soc.* (C), p. 1491-93, 1967.

(Continued)

Primary Examiner — James Jones
(74) Attorney, Agent, or Firm — Norton Rose Fulbright US LLP

(57) ABSTRACT

The present invention relates to a group of novel electrochromic materials. More specifically, it relates to electrochromic materials based on either single or two-core viologen systems and the use of these viologen systems as a variable transmittance medium for the manufacture of an optical article, such as an ophthalmic lens.

21 Claims, No Drawings

(56) References Cited

FOREIGN PATENT DOCUMENTS

| WO | WO 2015/040029 | 3/2015 |
| WO | WO 2015/040030 | 3/2015 |
| WO | WO 2015/040031 | 3/2015 |

OTHER PUBLICATIONS

International Search Report and Written Opinion issued in PCT/EP2014/069731, dated Apr. 10, 2015.
International Search Report and Written Opinion issued in PCT/EP2014/069737, dated Apr. 15, 2015.
International Search Report and Written Opinion issued in PCT/EP2014/069730, dated Apr. 15, 2015.
International Search Report and Written Opinion issued in PCT/EP2014/069734, dated Oct. 6, 2014.

\* cited by examiner

ELECTROCHROMIC SINGLE AND TWO-CORE VIOLOGENS AND OPTICAL ARTICLES CONTAINING THEM

CROSS-REFERENCE TO RELATED APPLICATIONS

This application is a national phase application under 35 U.S.C. §371 of International Application No. PCT/EP2014/069737 filed 16 Sep. 2014, which claims priority to European Patent Application No. 13184771.7 filed 17 Sep. 2013. The entire contents of each of the above-referenced disclosures is specifically incorporated by reference herein without disclaimer.

The present invention relates to a group of novel electrochromic materials. More specifically, it relates to electrochromic materials based on either single or two-core viologen systems and the use of these viologen systems as a variable transmittance medium for the manufacture of an optical article, such as an ophthalmic lens.

Electrochromism is a well known physical phenomenon which is observed with certain classes of chemical compounds that change reversibly colour when a voltage is applied to them. The material undergoes reversible changes in optical properties by oxidation and reduction. Usually the electrochromic material may be colourless when an electric field is not applied and may be coloured when an electric field is applied.

An electrochromic device, i.e. a device containing electrochromic compounds, the absorbance of which depends only on the presence of an electric field, can thus have two states, i.e a coloured state (when electrically activated) and a bleached state (in the inactive state). The optical transmission properties of the device depend on the nature of the electrochromic compounds.

There remains a need for improving electrochromic materials in order to use them as transparent media for forming high quality articles, in particular high quality ophthalmic lenses, while keeping electrochromic properties and having a wide range of colours.

After conducting extensive research, the present inventors provide novel electrochromic compounds exhibiting not only good electrochromic properties such as high absorption of the visible light in the coloured state, fast colouring and fading rates, long-term stability but also can be incorporated easily in a cellule to form for instance an electrochromic lens.

The applicants now have synthesized a group of novel electrochromic single and two-core viologens.

The present invention relates to electrochromic compounds of formula (I) as defined below.

The present invention also relates to an electrochromic composition comprising at least one compound of formula (I).

Finally, the present invention relates to an electrochromic device comprising said electrochromic composition, such as ophthalmic lens.

Thus, the present invention concerns electrochromic compounds represented by formula (I):

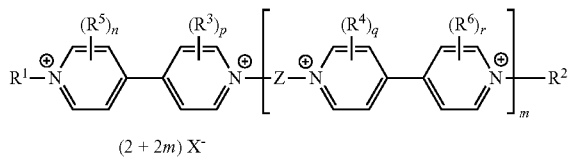

(I)

$(2 + 2m)\ X^-$ wherein:
Z is selected from:
  alkylene;
  cycloalkylene; and
  a bivalent group of formula —$R^7$—Y—$R^8$—, wherein $R^7$ and $R^8$ are each independently selected from single bond, alkylene and cycloalkylene, and
    Y is selected from arylene, cycloalkylene, heteroarylene, arylene-arylene or arylene-CR'R''-arylene wherein R' and R'' form together with the carbon to which they are linked a carbocyclic group;
  wherein said alkylene, cycloalkylene, arylene, heteroarylene, and carbocyclic groups may be substituted by one or more substituents selected from halogen, alkyl, alkoxy, alkylthio, hydroxyalkyl, acyloxy, cycloalkyl, aryl, substituted aryl, aryloxy, heteroaryl and substituted heteroaryl;
m is 0 or 1;
$R^1$ and $R^2$ are each independently selected from $C_6$-$C_7$ alkyl and optionally substituted phenyl,
with the provisions that:
when Y is arylene-arylene or arylene-alkylene-arylene, then $R^1$ and $R^2$ are not phenyl; when m is 0, then $R^1$ and $R^2$ are each independently selected from optionally substituted phenyl groups and at least one of $R^1$ and $R^2$ is selected from substituted phenyl groups, preferably $R^1$ and $R^2$ are each independently selected from substituted phenyl groups;
$R^3$, $R^4$, $R^5$ and $R^6$ are each independently selected from H, alkyl, alkoxy, alkylthio, haloalkyl, haloalkoxy, haloalkylthio, polyalkylenoxy, alkoxycarbonyl, aryl, substituted aryl, heteroaryl and substituted heteroaryl, wherein the alkyl group may be substituted by one or more substituents selected from alkoxy, cycloalkyl, aryl, substituted aryl, heteroaryl and substituted heteroaryl;
n, p, q and r are each independently an integer from 0 to 4, wherein when n, p, q and r are two or more, each of the $R^3$, each of the $R^4$, each of the $R^5$ or each of the $R^6$ may be identical or different; and
$X^-$ is a counterion.

The expression "alkylene" represents any divalent radical of a linear or branched hydrocarbon chain comprising 1 to 12 carbon atoms. Examples of $C_1$-$C_{12}$ alkylene groups include $C_1$-$C_4$ alkylene groups such as —$CH_2$—, —$(CH_2)_2$—, —$(CH_2)_3$—, —$(CH_2)_4$—, —$CH(CH_3)$—, —$CH(CH_3)$—$CH_2$—, —$CH_2$—$CH(CH_3)$—, —$(CH_2)_2$—$CH(CH_3)$—, —$CH_2$—$CH(CH_3)$—$CH_2$— or —$CH(CH_3)$—$(CH_2)_2$—, as well as —$(CH_2)_5$—, —$(CH_2)_6$—, —$(CH_2)_2$—$CH(CH_3)$—$(CH_2)_2$—, —$(CH_2)_3$—$CH(CH_3)$—$CH_2$—, —$(CH_2)_7$—, —$(CH_2)_8$—, —$(CH_2)_9$—, —$(CH_2)_{10}$—, —$(CH_2)_{11}$—, —$(CH_2)_{12}$.

The expression "cycloalkylene" represents any any divalent radical of a monocyclic or bicyclic 3 to 12 membered carbocycle. Examples of $C_3$-$C_{12}$ alkylene groups include cyclopropylene, cyclopentylene, cyclohexylene, cycloheptylene, and decahydronaphthylene.

The expression "arylene" represents any divalent radical of an aromatic hydrocarbon comprising 6 to 18 carbon atoms. Examples of $C_6$-$C_{18}$ arylene groups include phenylene, naphthylene, anthracenylene and phenanthrenylene.

The expression "carbocyclic group" represents any monocyclic or fused polycyclic hydrocarbon rings comprising 3 to 20 carbon atoms and which may comprise one or more unsaturations. Examples of $C_3$-$C_{20}$ carbocyclic groups include $C_{10}$-$C_{20}$ fused hydrocarbon rings which may comprise one or more unsaturations, such as cyclohexenylene, indene, fluorene.

The expression "halogen" includes F, Cl, Br or I. Preferred halogens are F and Cl.

The expression "alkyl" represents any monovalent radical of a linear or branched hydrocarbon chain comprising 1 to 18 carbon atoms. Examples of $C_1$-$C_{18}$ alkyl groups include $C_1$-$C_4$ alkyl groups such as methyl, ethyl, n-propyl, i-propyl, n-butyl, i-butyl, s-butyl or t-butyl, $C_6$-$C_8$ alkyl groups such as n-hexyl, n-heptyl or n-octyl, as well as n-pentyl, 2-ethylhexyl, 3,5,5-trimethylhexyl, n-nonyl, n-decyl, n-undecyl, n-dodecyl or n-Octadecyl.

The expression "alkoxy" represents a radical of formula —OR wherein R is a $C_1$-$C_{12}$ alkyl. Examples of $C_1$-$C_{12}$ alkoxy groups include $C_1$-$C_6$ alkoxy groups such as —$OCH_3$, —$OCH_2CH_3$ or $O(CH_2)_5CH_3$.

The expression "cycloalkyl" represents any monovalent radical of a monocyclic or bicyclic 3 to 12 membered saturated carbocycle. Examples of $C_3$-$C_{12}$ cycloalkyl groups include cyclopropyl, cyclopentyl and cyclohexyl.

The expression "aryl" represents any monovalent radical of an aromatic hydrocarbon comprising 6 to 18 carbon atoms. Examples of $C_6$-$C_{18}$ aryl groups include phenyl, naphthyl, anthracenyl and phenanthrenyl.

The expression "substituted aryl" represents any $C_6$-$C_{18}$ aryl group as defined above substituted by one or more substituents selected from halogen, alkyl, alkoxy, alkynyl haloalkyl, haloalkoxy, alkoxycarbonyl, alkanoyl, aroyl, formyl, nitrile, nitro, amido, alkylthio, alkylsulfinyl, alkylsulfonyl, arylthio, arylsulfinyl, arylsulfonyl, amino, alkylamino, arylamino, dialkylamino and diarylamino. Preferably, the substituents are selected from bulky or electron withdrawing groups. Examples of substituted $C_6$-$C_{18}$ aryl groups include substituted phenyl groups such as p-methylphenyl, o-t-butylphenyl, p-trifluoromethoxyphenyl, o-trifluoromethoxyphenyl, m-cyanophenyl, o-i-propylphenyl, 2,4-dinitrophenyl, 2,6-diisopropylphenyl or 3,5-dicyanophenyl.

The expression "aryloxy" represents a radical of formula —OR wherein R is a $C_6$-$C_{18}$ aryl. Examples of $C_1$-$C_{12}$ aryloxy groups include phenyloxy and naphthyloxy.

The expression "heteroaryl" represents any monovalent radical of a monocyclic or bicyclic 5 to 10 membered aromatic group comprising from 1 to 3 heteroatoms independently selected from oxygen, nitrogen and sulfur. Examples of $C_5$-$C_{10}$ heteroaryl groups include furyl, thienyl, pyrrolyl, pyrazoyl, imidazolyl, isoxazolyl, isothiazoyl, thiazolyl, oxazolyl, 1,2,3-triazolyl, 1,2,4-triazolyl, 1-benzofuryl, 1-benzothienyl, indolyl, benzimidazolyl, indazolyl, 1,2-benzisoxazolyl, 2,1-benzisoxazolyl, 1,2-benzisothiazolyl, 2,1-benzisothiazolyl, benzothiazolyl, benzoxazolyl, benzotriazolyl, pyridyl, quinolinyl, isoquinolinyl, pyridazinyl, cinnolinyl, phthalazinyl, pyrimidinyl, quinazolinyl, pyrazinyl and quinoxalinyl.

The expression "heteroarylene" represents any divalent radical of a monocyclic or bicyclic 5 to 10 membered aromatic group comprising from 1 to 3 heteroatoms independently selected from oxygen, nitrogen and sulfur. Examples of $C_5$-$C_{10}$ heteroarylene groups include furylene, thienylene, pyrrolylene, pyrazoylene, imidazolylene, isoxazolylene, isothiazoylene, thiazolylene, oxazolylene, 1,2,3-triazolylene, 1,2,4-triazolylene, 1-benzofurylene, 1-benzothienylene, indolylene, benzimidazolylene, indazolylene, 1,2-benzisoxazolylene, 2,1-benzisoxazolylene, 1,2-benzisothiazolylene, 2,1-benzisothiazolylene, benzothiazolylene, benzoxazolylene, benzotriazolylene, pyridylene, quinolinylene, isoquinolinylene, pyridazinylene, cinnolinylene, phthalazinylene, pyrimidinylene, quinazolinylene, pyrazinylene and quinoxalinylene.

The expression "substituted heteroaryl" represents any heteroaryl group as defined above substituted by one or more substituents selected from alkyl, alkoxy, alkoxycarbonyl, alkanoyl, aroyl, formyl, nitrile, nitro, amido, alkylthio, alkylsulfinyl, alkylsulfonyl, arylthio, arylsulfinyl, arylsulfonyl, amino, alkylamino, arylamino, dialkylamino and diarylamino. Preferably, the substituents are selected from bulky or electron withdrawing groups. Examples of substituted $C_5$-$C_{10}$ heteroaryl groups include 4-methylthienyl, 5-methyl-2-thienyl, 6-methyl-2-pyridyl, N-methylpyrrol-2-yl and N-phenylindol-3-yl.

The expression "haloalkyl" represents any $C_1$-$C_{12}$ alkyl group substituted by one or more halogen atom such as F or Cl. Examples of $C_1$-$C_{12}$ haloalkyl groups include $C_1$-$C_{12}$ perhaloalkyl groups, in particular $C_1$-$C_4$ perhaloalkyl groups such as —$CF_3$, as well as $C_1$-$C_{12}$ (perhaloalkyl)alkyl groups, in particular ($C_1$-$C_4$ perhaloalkyl)-($C_1$-$C_4$ alkyl) groups such as —$CH_2CF_3$.

The expression "haloalkoxy" represents a radical of formula —OR wherein R is a $C_1$-$C_{12}$ haloalkyl. Examples of $C_1$-$C_{12}$ haloalkoxy include $C_1$-$C_{12}$ perhaloalkoxy groups, in particular $C_1$-$C_4$ perhaloalkoxy groups such as —$OCF_3$, as well as $C_1$-$C_{12}$ (perhaloalkyl)alkoxy groups, in particular ($C_1$-$C_4$ perhaloalkyl)-($C_1$-$C_4$ alkoxy) groups such as —$OCH_2CF_3$.

The expression "alkylthio" represents a radical of formula —SR wherein R is a $C_1$-$C_{12}$ alkyl. Examples of $C_1$-$C_{12}$ alkylthio groups include —$SCH_3$ and —$SCH_2CH_3$.

The expression "haloalkylthio" represents a radical of formula —SR wherein R is a $C_1$-$C_{12}$ haloalkyl. Examples of $C_1$-$C_{12}$ haloalkoxy groups include $C_1$-$C_{12}$ perhaloalkylthio groups, in particular $C_1$-$C_4$ perhaloalkylthio groups such as —$SCF_3$, as well as $C_1$-$C_{12}$ (perhaloalkyl)alkylthio groups, in particular ($C_1$-$C_4$ perhaloalkyl)-($C_1$-$C_4$ alkylthio) groups such as —$SCH_2CF_3$.

The expression "hydroxyalkyl" represents any $C_1$-$C_{12}$ alkyl group substituted by one or more hydroxyl groups. Examples of $C_1$-$C_{12}$ hydroxyalkyl groups include —$CH_2OH$ and —$CH_2CH_2OH$.

The expression "acyloxy" represents a radical of formula —OC(O)R wherein R is a $C_1$-$C_{12}$ alkyl. Examples of $C_1$-$C_{12}$ acyloxy groups include —$OC(O)CH_3$ and —$OC(O)CH_2CH_3$.

The expression "polyalkylenoxy" represents a radical of formula —O(R'O)$_m$R wherein R' is a $C_1$-$C_{12}$ alkylene, R is a $C_1$-$C_{12}$ alkyl and m is an integer from 1 to 12. Examples of poly($C_1$-$C_{12}$ alkylenoxy) groups include $OCH_2CH_2OCH_3$.

The expression "alkoxycarbonyl" represent a radical of formula —C(O)OR wherein R is a $C_1$-$C_{18}$ alkyl. Examples of $C_1$-$C_{18}$ alkoxycarbonyl groups include $C_1$-$C_4$ alkoxycarbonyl groups such as —$C(O)OCH_3$ and —$C(O)OC_2H_5$.

In formula (I), Z, called "the central core", is preferably selected from $C_1$-$C_{12}$ alkylene, $C_3$-$C_7$ cycloalkylene, $C_3$-$C_{14}$ arylene, $C_5$-$C_{10}$ heteroarylene, ($C_1$-$C_4$ alkylene)-($C_3$-$C_{14}$ arylene), ($C_1$-$C_4$ alkylene)-($C_3$-$C_{14}$ heteroarylene), ($C_1$-$C_4$ alkylene)-($C_3$-$C_{14}$ arylene)-($C_1$-$C_4$ alkylene), ($C_1$-$C_4$ alkylene)-($C_3$-$C_{14}$ heteroarylene)-($C_1$-$C_4$ alkylene), ($C_3$-$C_{14}$ arylene)-($C_3$-$C_{14}$ arylene), ($C_1$-$C_4$ alkylene)-($C_3$-$C_{14}$ arylene)-($C_3$-$C_{14}$ arylene)-($C_1$-$C_4$ alkylene) and ($C_3$-$C_{14}$ arylene)-(CR'R")-($C_3$-$C_{14}$ arylene) wherein R' and R" form together with the carbon to which they are linked a $C_3$-$C_{20}$ carbocyclic group; wherein the arylene and cycloalkylene groups may be substituted by one or more substituents selected from halogen, $C_1$-$C_4$ alkyl, $C_1$-$C_4$ alkoxy and $C_3$-$C_7$ cycloalkyl and the alkylene groups may be substituted by one or more substituents selected from halogen, $C_3$-$C_{14}$ alkyl, $C_1$-$C_{12}$ alkoxy, $C_2$-$C_{12}$ acyloxy, $C_1$-$C_{12}$ hydroxyalkyl, $C_3$-$C_{12}$ cycloalkyl, phenyl, phenyloxy and substituted phenyl. In particular, substituted alkylene include —$CH_2$(CR$^a$R$^b$)CH$_2$— wherein R$^a$ and R$^b$ may be independently selected from H, $C_3$-$C_{14}$ alkyl, $C_3$-$C_{12}$ cycloalkyl, (cycloalkyl)methyl, aryl, substituted aryl, arylalkyl such as benzyl or phenyl($C_2$-$C_7$ alkyl), phenyloxyethyl, substituted arylalkyl, $C_1$-$C_{12}$ alkoxy, $C_2$-$C_{12}$ acyloxy, $C_1$-$C_{12}$ hydroxyalkyl, and $C_1$-$C_{12}$ alkoxymethyl.

More preferably, Z is selected from $C_1$-$C_{12}$ alkylene, aryl substituted $C_1$-$C_{12}$ alkylene, phenylene, naphthylene, ($C_1$-$C_4$ alkylene)-phenylene-($C_1$-$C_4$ alkylene), ($C_1$-$C_4$ alkylene)-naphthylene-($C_1$-$C_4$ alkylene) such as naphthylene bis(m-ethylene), quinoxaline-2,3-diyl, ($C_1$-$C_4$ alkylene)-quinoxaline-2,3-diyl-($C_1$-$C_4$ alkylene) such as quinoxaline-2,3-diylbis(methylene), phenylene-phenylene, ($C_1$-$C_4$ alkylene)-phenylene-phenylene-($C_1$-$C_4$ alkylene) and phenylene-fluorenylene-phenylene. For example, Z may be selected from —$CH_2$—, —$(CH_2)_2$—, —$(CH_2)_3$—, —$(CH_2)_4$—, —$(CH_2)_5$—, —$CH_2$—CH($CH_3$)—$CH_2$—, —$CH_2$—CH($CH_2$Phenyl)-$CH_2$—, —$(CH_2)_2$—CH($CH_3$)—$CH_2$—, —$(CH_2)_3$—CH($CH_3$)—$CH_2$—, —$(CH_2)_2$—CH($CH_3$)—$(CH_2)_2$—,

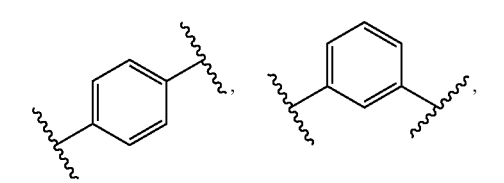,

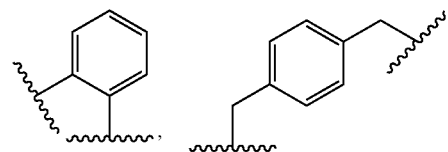,

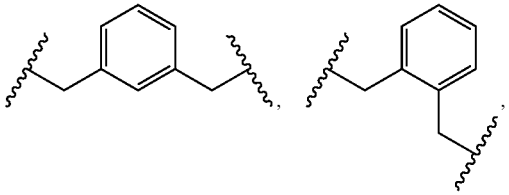,

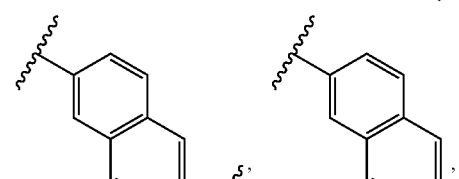,

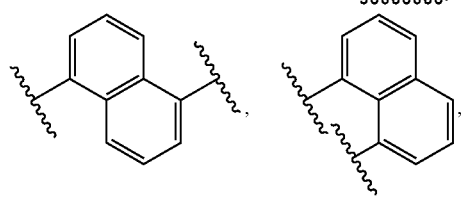,

-continued

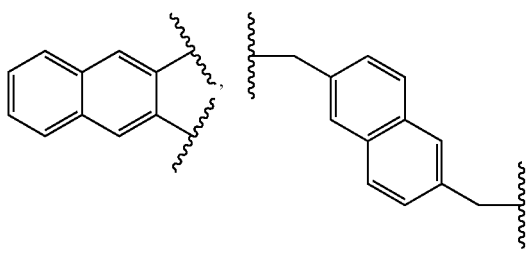,

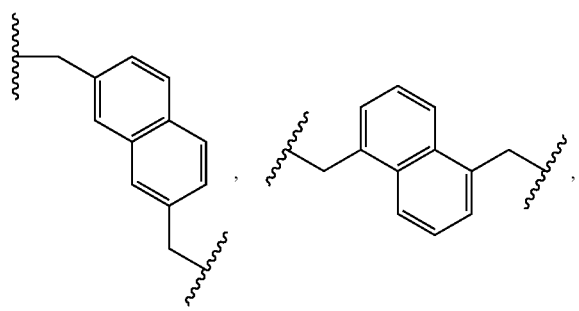,

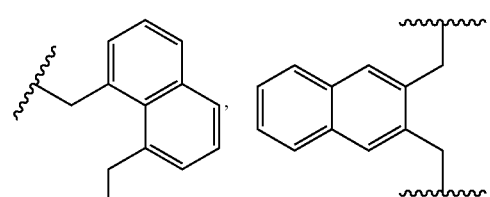,

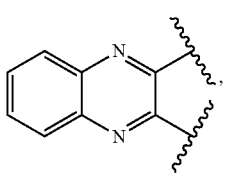,

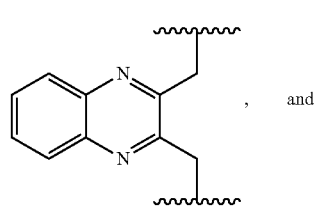, and

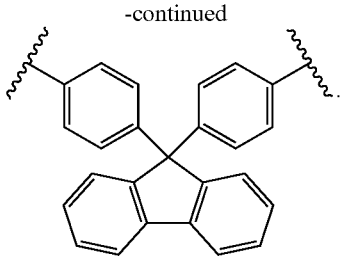

$R^3$, $R^4$, $R^5$ and $R^6$ are preferably each independently selected from $C_1$-$C_4$ alkyl, $C_1$-$C_4$ alkoxycarbonyl, alkanoyl, aroyl, nitrile, alkylsulfonyl, arylsulfonyl, aryl and heteroaryl, wherein the aryl and heteroaryl may be substituted by one or more substituents selected from $C_1$-$C_4$ alkyl and $C_1$-$C_4$ haloalkyl. Aryl, heteroaryl, substituted aryl and substituted heteroaryl are particularly preferred, and more particularly optionally substituted phenyl such as phenyl, tolyl and cumyl, because they induce a decrease of the activation potential of the compounds of the invention. Moreover, the steric hindrance provided by the presence of such substituents on the viologen cores of the compounds of the invention is believed to prevent π- πinteractions between the aromatic viologen cores which is the cause of the stacking phenomenon on or near the electrode surface. For example, $R^3$, $R^4$, $R^5$ and $R^6$ may be independently selected from methyl, ethoxycarbonyl, phenyl, p-methylphenyl and p-trifluoromethylphenyl, preferably from phenyl, p-methylphenyl and p-trifluoromethylphenyl.

n, p, q and r are each independently an integer from 0 to 4, wherein when n, p, q and r are two or more, each of the $R^3$, each of the $R^4$, each of the $R^5$ or each of the $R^6$ may be identical or different. Preferably, n and r are 0 when at least one of p and q is an integer from 1 to 4, and conversely p and q are 0 when at least one of n and r is an integer from 1 to 4. In a preferred embodiment, n and r are 0 and p and q are 2. In such an embodiment the two $R^3$ substituents, respectfully the two $R^4$ substituents, are identical. The two $R^3$ substituents, respectfully the two $R^4$ substituents are preferably located meta to each other and are all ortho position relative to the central core Z. Moreover, the $R^3$ substituents may be similar or different from the $R^4$ substituents. In another embodiment, n, p, q and r are 0.

The counterion $X^-$ may be any anion that maintains electric neutrality of the viologen compounds of formula (I). $X^-$ is preferably selected from halide, preferably fluoride and chloride, tetrafluoroborate, tetraphenylborate, hexafluorophosphate, nitrate, methanesulfonate, trifluoromethane sulfonate, toluene sulfonate, hexachloroantimonate, bis(trifluoromethanesulfonyl)imide, perchlorate, acetate and sulfate.

In a first embodiment, the present invention relates to compounds of formula (I) wherein Z, $R^3$, $R^4$, $R^5$, $R^6$, n, p, q, r and $X^-$ are as defined above, m is 1 and $R^1$ and $R^2$ are $C_6$-$C_7$ alkyl, preferably $C_6H_{13}$, more preferably n-$C_6H_{13}$. Applicant has found that $C_6$-$C_7$ alkyl substituents have a good solubility in conventional solvents used in electrochromic compositions such as propylene carbonate while maintaining a fast fading rate to the bleached state. Indeed, $C_1$-$C_5$ alkyl substituted two-core viologen compounds are more difficult to solubilise in conventional solvents used in electrochromic compositions. On the contrary, higher alkyl substituted two-core viologen compounds have good solubility. However, when two-core viologen compounds are substituted with long chain alkyls having more than 7 carbon atoms the fading rate may decrease, which prevents a fast reversibility to the bleached state.

In a second embodiment, the present invention relates to compounds of formula (I) wherein Z, $R^3$, $R^4$, $R^5$, $R^6$, n, p, q, r and $X^-$ are as defined above and $R^1$ and $R^2$ are independently selected from optionally substituted phenyl groups, provided that when m is 0, $R^1$ and $R^2$ are not both phenyl, preferably neither $R^1$ nor $R^2$ are phenyl. In other words, $R^1$ and $R^2$ are each independently selected from optionally substituted phenyl groups and at least one of $R^1$ and $R^2$ is selected from substituted phenyl groups, preferably $R^1$ and $R^2$ are each independently selected from substituted phenyl groups. The inventors have observed that the presence of phenyl groups results in the stabilization of the compounds of the invention and, consequently, in a decrease of the activation potential, which corresponds to an increase of the reduction potential, of the viologen compounds. Optionally substituted phenyl groups are represented by formula (II):

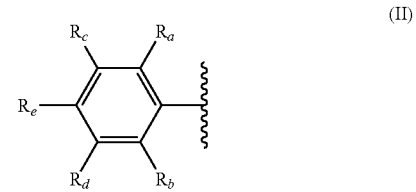

wherein $R_a$, $R_b$, $R_c$, $R_d$ and $R_e$ are each independently selected from:

H, halogen, cyano, nitro, alkyl, haloalkyl, haloalkoxy, (haloalkoxy)alkyl, arylalkyl, cycloalkyl, (cycloalkyl)alkyl and (heterocycloalkyl)alkyl, alkenyl, alkynyl, allyl, vinyl, aryl, substituted aryl, heteroaryl, substituted heteroaryl, —N(aryl)$_2$, —N(aryl)CO(aryl), —CO-aryl and —CO-substituted aryl;

—OR$^9$, —SR$^9$, —S(O)R$^9$, —S(O$_2$)R$^9$, —S(O$_2$)NR$^9$R$^{10}$, —NR$^9$R$^{10}$, —NR$^9$COR$^{10}$, —NR$^9$CO(aryl), —NR$^9$aryl, —CH$_2$OR$^9$, —CH$_2$SR$^9$, —CH$_2$R$^9$, —CO—R$^9$ and —CO$_2$R$^{10}$ wherein R$^9$ and R$^{10}$ are independently selected from H, alkyl, haloalkyl, arylalkyl, cycloalkyl, cycloalkylalkyl and heterocycloalkylalkyl;

—S(O$_2$)NR$^{11}$R$^{12}$ and —NR$^{11}$R$^{12}$, wherein R$^{11}$ and R$^{12}$ form together with the nitrogen atom to which they are linked a saturated 5 to 7 membered heterocycloalkyl which may comprising in addition to the nitrogen atom one further heteroatom selected from oxygen, nitrogen and sulfur, and which may be optionally substituted by one or two groups, identical or different, selected from halogen, —R$^9$, —OR$^9$, and —NR$^9$R$^{10}$, wherein R$^9$ and R$^{10}$ are as defined above;

—V—W—R$^{13}$ wherein:
V is selected from oxygen, —N(R$^9$)—, sulfur, —S(O)— and —S(O$_2$)— wherein R$^9$ is as defined above;
W is alkylene, which may be substituted by a group selected from halogen and alkoxy; and
R$^{13}$ is selected from —OR$^9$, —NR$^9$(alkyl) and —SR$^9$ wherein R$^9$ is as defined above; and OC(O)—R$^{14}$ wherein R$^{14}$ is selected from alkyl, haloalkyl, alkenyl, —W—R$^{13}$, and aryl group which may be substituted by 1 to 4 groups selected from halogen, —R$^9$, —OR$^9$, —SR$^9$, —NR$^9$R$^{10}$, —NR$^{11}$R$^{12}$, —CO—R[9], —CO$_2$R[9] wherein R[9], R[10], R[11], R[12], R[13] and W are as defined above.

In particular, $R_a$, $R_b$, $R_c$, $R_d$ and $R_e$ may be independently selected from H, halogen, cyano, nitro, hydroxyl, alkyl, preferably $C_4$-$C_{12}$ alkyl, haloalkyl, alkoxy, haloalkoxy, alkylthio, acyl, aroyl, alkoxycarbonyl, cycloalkyl, allyl, aryl, benzyl, and heteroaryl. In a particular embodiment, at least one of $R_a$, $R_b$, $R_c$, $R_d$ and $R_e$ is not H. Preferably, at least one of $R_a$, $R_b$, $R_c$, $R_d$ and $R_e$ is selected from halogen, cyano, nitro, hydroxyl, haloalkyl, haloalkoxy, alkoxycarbonyl, allyl, aryl and heteroaryl. Indeed, the inventors have found that such electron-withdrawing substituents stabilize the radical cation which results in a decrease of the activation potential. In a preferred embodiment, $R_e$ is H and at least one of $R_a$, $R_b$, $R_c$ and $R_d$ is not H, preferably at least one of $R_a$ and $R_b$ is not H.

In a preferred variant; in particular in the case where $R_1$ and $R_2$ are chosen to be different, then at least one of $R_1$ and $R_2$ is of Formula (II), wherein $R_e$ is H and at least one of $R_a$, $R_b$ $R_c$ and $R_d$ is not H, and may be independently selected from halogen, cyano, nitro, hydroxyl, $C_1$-$C_{12}$ alkyl, haloalkyl, alkoxy, haloalkoxy, alkoxycarbonyl, cycloalkyl, allyl, aryl and heteroaryl.

In another preferred variant; in particular in the case where $R_1$ and $R_2$ are chosen to be different, and when m is 0, then at least one of $R_1$ and $R_2$ is of Formula (II), wherein $R_e$ is H and at least one of $R_a$, $R_b$ $R_c$ and $R_d$ is not H, and may be independently selected from halogen, cyano, hydroxyl, $C_1$-$C_{12}$ alkyl, haloalkyl, alkoxy, haloalkoxy, alkoxycarbonyl, cycloalkyl, allyl, and heteroaryl.

In another variant, in particular in the case where $R_1$ and $R_2$ are chosen to be identical and when m is 0, $R_e$ is H and at least one of $R_a$, $R_b$ $R_c$ and $R_d$ is not H, and may be independently selected from halogen, cyano, nitro, hydroxyl, $C_4$-$C_{12}$ alkyl, haloalkyl, alkoxy, haloalkoxy, alkoxycarbonyl, cycloalkyl, allyl, aryl and heteroaryl.

In another variant, in particular when m=0, then $R_e$ is H and at least one of $R_a$, $R_b$ $R_c$ and $R_d$ is not H, and may be independently selected from halogen, cyano, hydroxyl, $C_4$-$C_{12}$ alkyl, haloalkyl, alkoxy, haloalkoxy, alkoxycarbonyl, cycloalkyl, allyl, and heteroaryl For example, at least one of $R_a$, $R_b$, $R_c$, $R_d$ and $R_e$ may be selected from methyl, i-propyl, t-butyl, cyano, trifluoromethoxy, preferably trifluoromethoxy. Thus, $R^1$ and $R^2$ may be independently selected from:

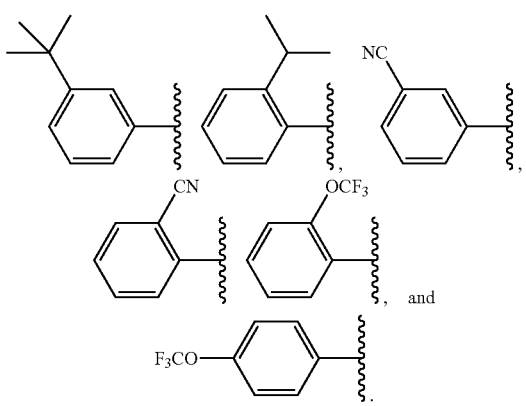

In a preferred embodiment, $R^1$ and $R^2$ are independently selected from substituted phenyl groups of formula (II) wherein $R_c$, $R_d$ and $R_e$ are H and $R_a$ and $R_b$ are as defined above provided that at least one of $R_a$ and $R_b$ is not H. In particular, $R^1$ and $R^2$ may be selected from:

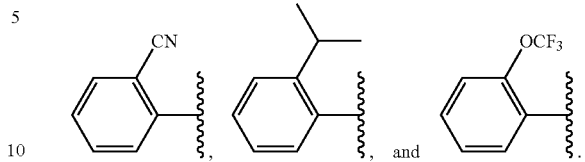

Indeed, the Applicant found that the presence of a substituent in the ortho position of the phenyl group results in a hypsochromic effect compared to the meta position, which itself provides a hypsochromic effect compared to the para position. Indeed the maximum wavelength $\lambda_{max}$ in the absorption spectrum for a similar compound is higher when the substituent is in the para position of the phenyl group, than in the meta position, and a fortiori than in the ortho position. Consequently, the present invention provides new electrochromic compounds that can have a wide range of colours in their coloured state, in particular in the low visible wavelength—i.e. a blue or green coloured state—, while presenting good stability and close oxido-reduction potential values to each other.

In a third embodiment, the present invention relates to compounds of formula (Ia):

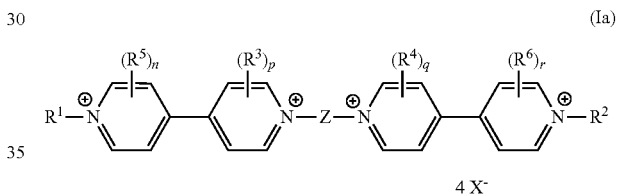

wherein Z, $R^1$, $R^2$, $R^3$, $R^4$, $R^5$, $R^6$, n, p, q, r and $X^-$ are as defined in formula (I). Preferably, $R^1$ and $R^2$ are independently selected from optionally substituted phenyl groups of formula (II) as defined in the second embodiment.

In a fourth embodiment, the present invention relates to compounds of formula (Ib):

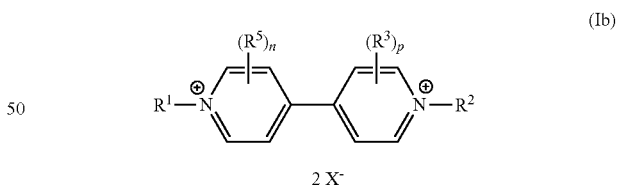

wherein Z, $R^3$, $R^4$, $R^5$, $R^6$, n, p, q, r and X are as defined in formula (I) and $R^1$ and $R^2$ are independently selected from optionally substituted phenyl groups of formula (II) as defined in the second embodiment provided that at least one of $R_a$, $R_b$, $R_c$, $R_d$ and $R_e$ is not H. In particular, in the case where $R_1$ and $R_2$ are chosen to be identical, $R_e$ is H and at least one of $R_a$, $R_b$ $R_c$ and $R_d$ is not H, and may be independently selected from halogen, cyano, nitro, hydroxyl, $C_4$-$C_{12}$ alkyl, haloalkyl, alkoxy, haloalkoxy, alkoxycarbonyl, cycloalkyl, allyl, aryl and heteroaryl.

In a particularly preferred embodiment, the compounds of the present invention are selected from the group consisting of:

| Compound | Formula |
|---|---|
| 1-1 | 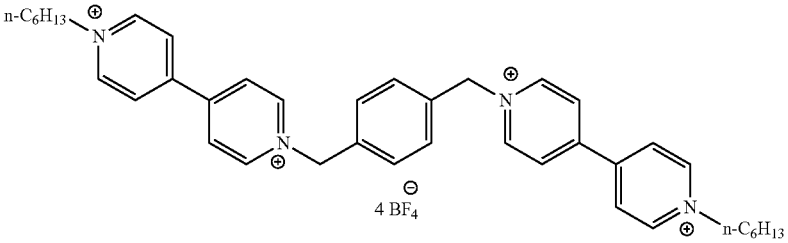 |
| 1-2 |  |
| 1-3 | 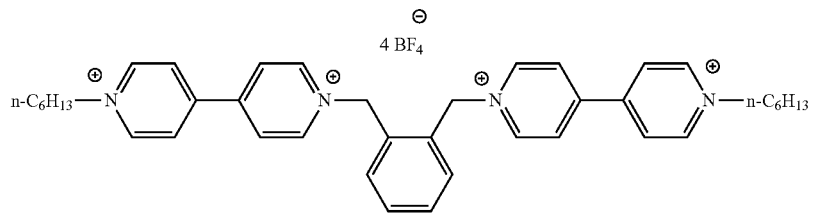 |
| 1-4a | 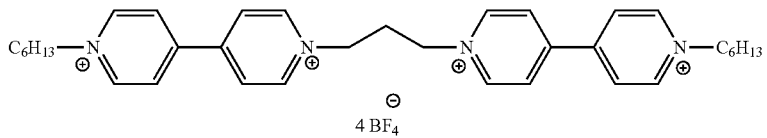 |
| 1-4b | 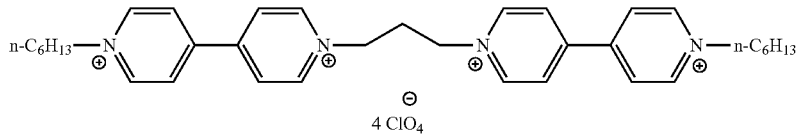 |
| 1-5 | 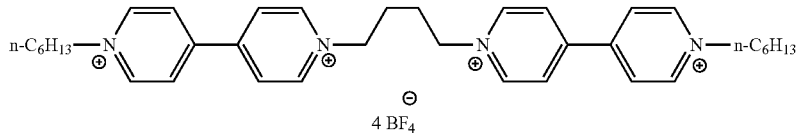 |
| 2-1 | 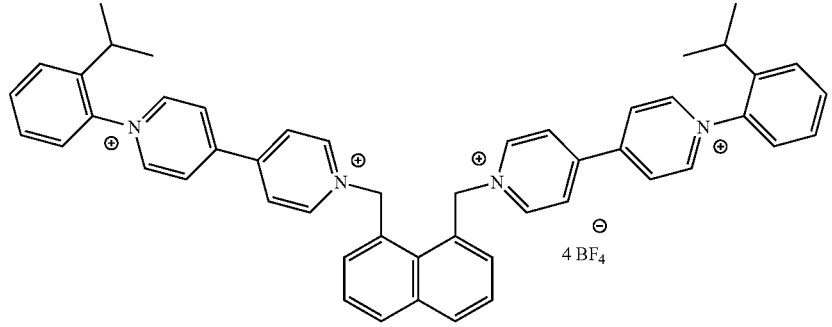 [SMILES: CC(C)c1ccccc1-[n+]1ccc(-c2cc[n+](Cc3cccc4cccc(C[n+]5ccc(-c6cc[n+](-c7ccccc7C(C)C)cc6)cc5)c34)cc2)cc1] |

-continued
| Compound | Formula |
|---|---|
| 2-2 | 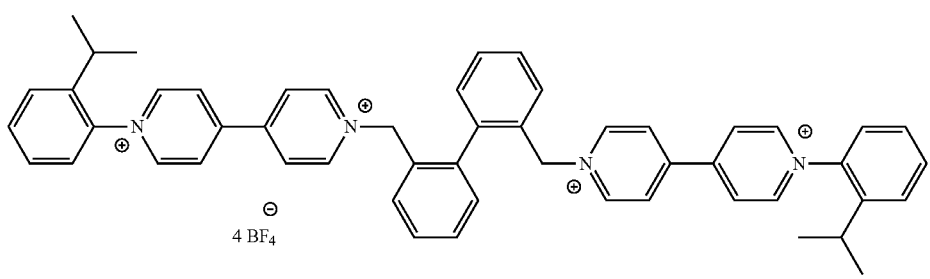 4 BF$_4^{\ominus}$ |
| 2-3 | 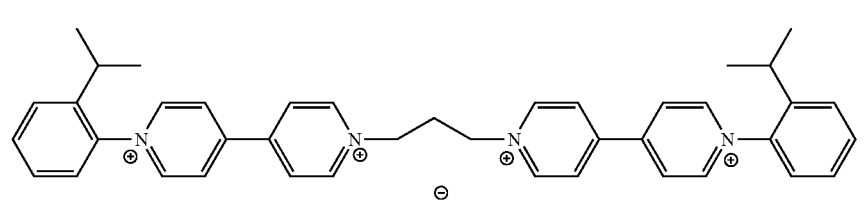 4 BF$_4^{\ominus}$ |
| 2-4 | 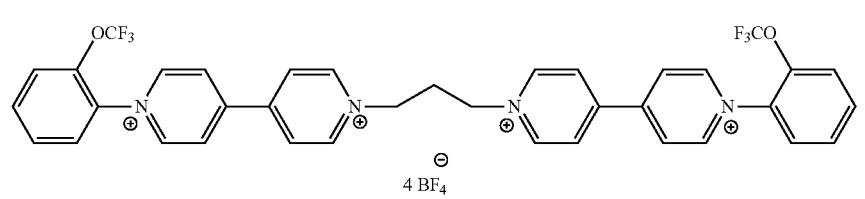 [SMILES: FC(F)(F)Oc1ccccc1-[n+]1ccc(-c2cc[n+](CCC[n+]3ccc(-c4cc[n+](-c5ccccc5OC(F)(F)F)cc4)cc3)cc2)cc1] 4 BF$_4^{\ominus}$ |
| 2-5 | 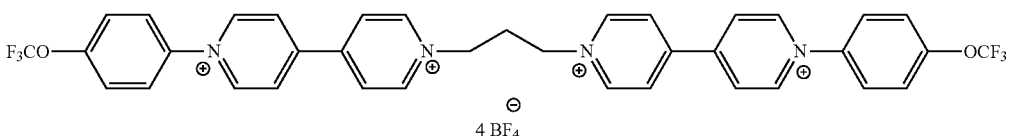 4 BF$_4^{\ominus}$ |
| 2-6 | 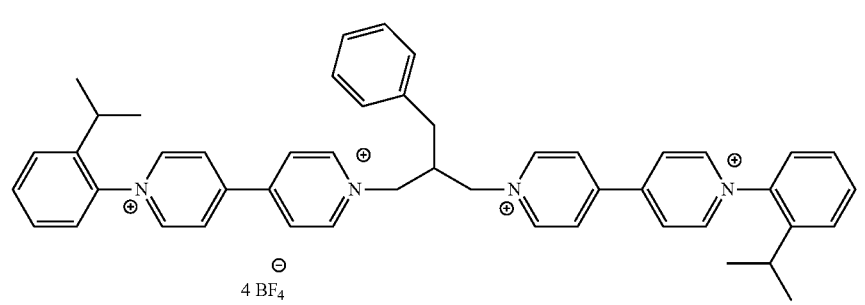 4 BF$_4^{\ominus}$ |
| 2-7 | 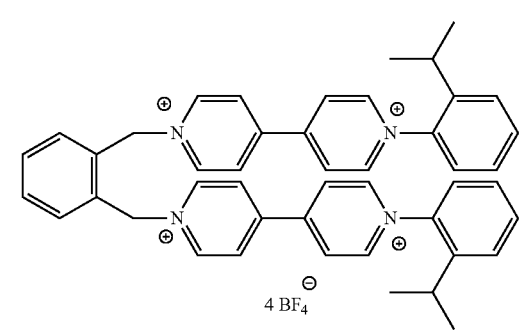 4 BF$_4^{\ominus}$ |

| Compound | Formula |
|---|---|
| 2-8 | 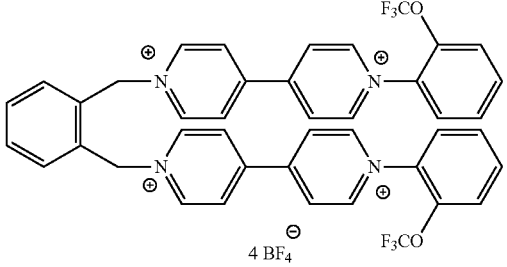 |
| 2-9 | 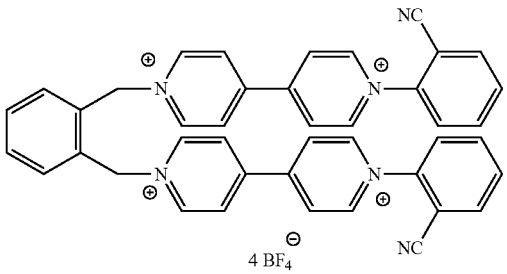 |
| 2-10 | 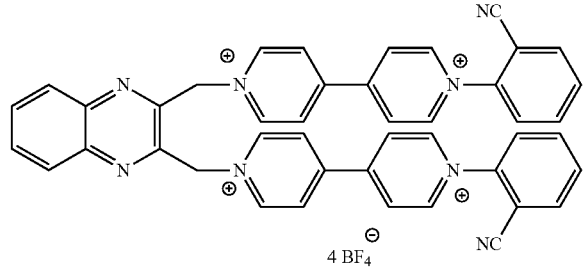 |
| 2-11 | 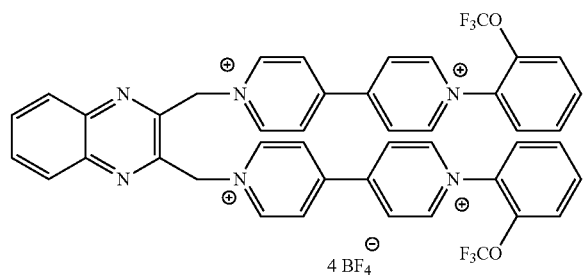 |
| 2-12 | 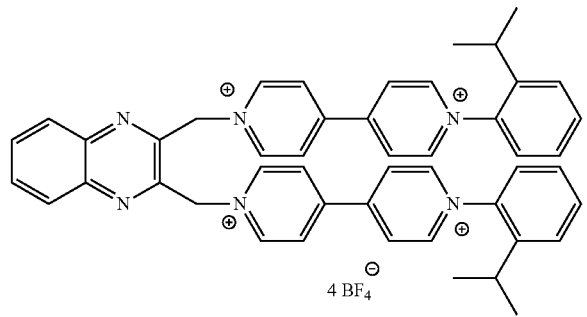 |

| Compound | Formula |
|---|---|
| 2-13 | 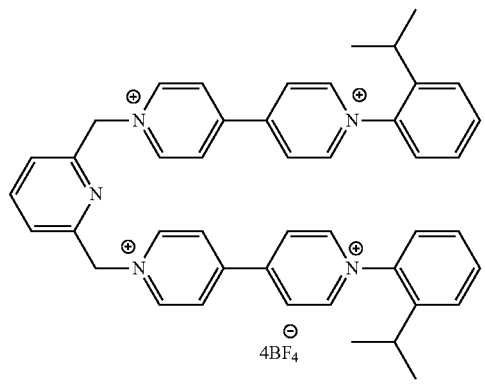 [SMILES: CC(C)c1ccccc1-[n+]1ccc(-c2cc[n+](Cc3cccc(C[n+]4ccc(-c5cc[n+](-c6ccccc6C(C)C)cc5)cc4)n3)cc2)cc1] |
| 3-1 | 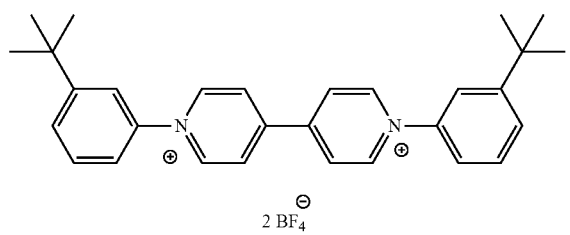 |
| 3-2 | 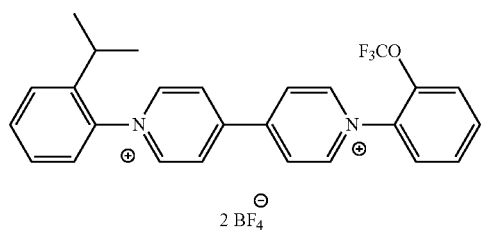 |
| 3-3 | 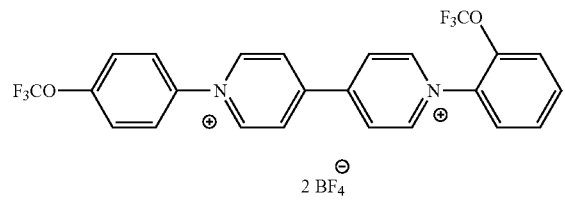 |
| 3-4 | 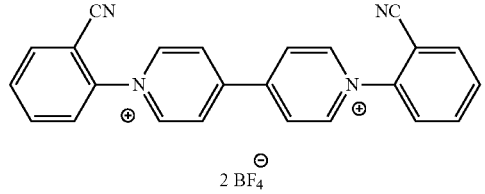 |

| Compound | Formula |
|---|---|
| 3-5 | 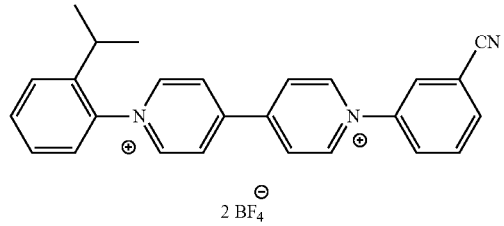<br>2 BF$_4^\ominus$ |
| 3-6 | 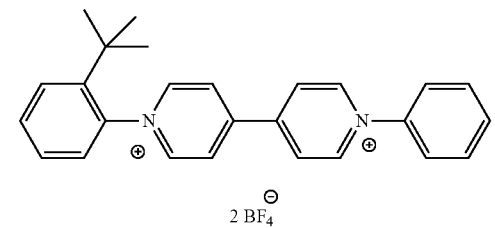<br>2 BF$_4^\ominus$ |
| 3-7 | 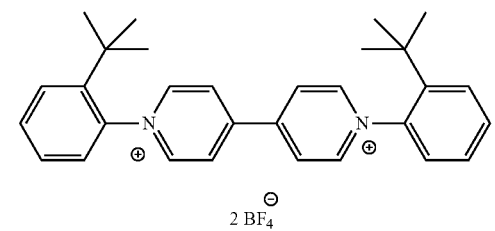<br>2 BF$_4^\ominus$ |
| 3-8 | 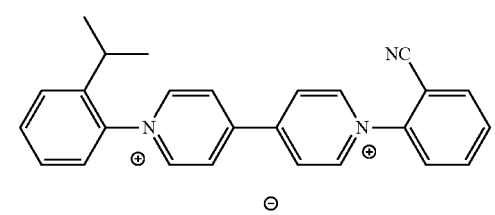<br>2 BF$_4^\ominus$ |

Compounds represented by formula (I) may be prepared according to various methods well known in the art. However, the inventors have found a particularly advantageous method for preparing compounds of formula (I), in particular compounds of formula (Ia) having substituted phenyl terminal groups.

Therefore, the present invention relates to a method for preparing a compound of formula (Ia), comprising the step (i) of alkylation of two bipyridinium salts having non-nucleophilic counterion, such as a tetrafluoroborate as depicted by (1) or (1'), with a bifunctional alkylating agent of formula ZL$_2$ in which the leaving group L is selected from sufonate and carboxylate groups such as methanesulfonate, p-toluenesulfonate, p-nitrobenzoate, trifluoromethanesulfonate (triflate), nonafluorobutanesulfonate (nonaflate) and pentafluorobenzenesulfonate. Of these, triflates are preferred, giving the mixed triflate tetrafluoroborate salt. Subsequent step (ii) is an anion exchange with an aqueous, such as aqueous NaBF$_4$, giving the double viologen product (Ia) as shown below in Scheme A.

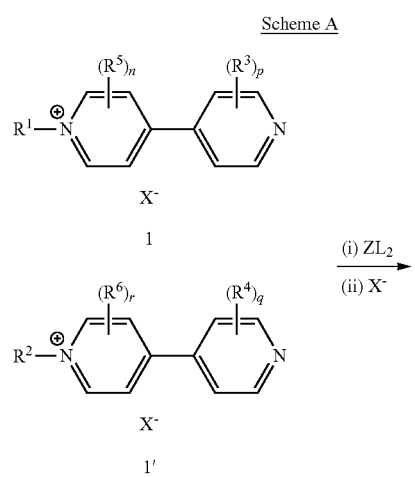

Scheme A

-continued

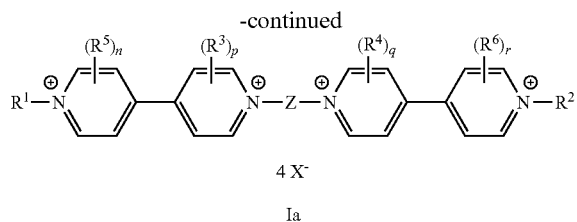

Ia

In Scheme A, Z is a central core as defined above, and $R^1$, $R^2$, $R^3$, $R^4$, $R^5$, $R^6$ are as defined above.

Further examples of synthesis of compounds according to the present invention are illustrated below.

The present invention also relates to electrochromic compositions comprising at least one compound of formula (I) as defined above as an oxidizing electrochromic compound. One or more additional oxidizing electrochromic compounds can be added to the composition of the invention so as to adapt the colour or the intensity of the coloured state of the composition. Said additional compound can be another compound of formula (I) or a different compound such as compatible dyes or pigments. For example, the additional oxidizing electrochromic compound can be selected from alkylviologens, arylviologens, alkylarylviologens or anthraquinone and derivatives. Preferably, the additional compound has a redox potential close to the compound of formula (I). The composition also comprises at least one reducing compound. The reducing compound can be also an electrochromic compound. Example of reducing compounds include 5,10-dihydrophenazine, phenothiazine, phenoxazine, N,N,N',N'-tetramethyl-p-phenylenediamine, thioanthrene, tetrathiafulvalene, ferrocene and their derivatives.

The composition of the invention may comprise a fluid, mesomorphous or gel host medium in which the electrochromic compounds are preferably dissolved. The fluid or mesomorphous host medium is preferably selected from the group consisting of organic solvents, liquid crystals, polymers or liquid crystal polymers and mixtures thereof.

Suitable solvents are redox-inert solvents which cannot react with the electrochromic compounds of the composition. Examples of suitable solvents are ethylene carbonate, propylene carbonate, γ-butyrolactone, γ-valerolactone, acetonitrile, propionitrile, benzonitrile, glutaronitrile, methylglutaronitrile, dimethylformamide, N-methylpyrrolidone, sulfolane, 3-methyl sulfolane, benzene, toluene, methyl ethyl ketone, acetone, ethanol, tetrahydrofurfuryl alcohol, 2-methoxyethyl ether, xylene, cyclohexane, 3-methylcyclohexanone, ethyl acetate, ethyl phenylacetate, tetrahydrofuran, methanol, methyl propionate, ethylene glycol, ethylene carbonate, ionic liquids, and mixtures thereof. Preference is given to carbonate and particularly propylene carbonate.

The liquid crystal medium that may be used in the present invention includes, without being limited to, such materials as nematic or chiral nematic media.

The polymers that may be used in the present invention includes, without being limited to polymers which are soluble with the solvent, in particular PMMA or other acrylate polymers, polyurethane, polyethylene oxide, polypropylene oxide, polyvinyl acetate, poly(N-vinyl pyrrolidone), and polyvinylidene fluoride.

Alternatively a polymeric liquid crystal medium can be used as the host material. These liquid crystals, polymer polymeric liquid crystal media are generally used in combination with an organic solvent, for example one of the organic solvents mentioned above.

The present invention also relates to an electrochromic device comprising a compound of formula (I) or a composition according to the invention. Said device may be selected from an optical article, preferably an optical lens, or an optical filter, a window, preferably an aircraft window, a visor, a mirror and a display, in particular a segmented or matrix display. Preferably, the device of the invention is an optical article, more preferably an optical lens, and even more preferably an ophthalmic lens.

Non-limiting examples of ophthalmic lens include corrective and non-corrective lenses, including single vision or multi-vision lenses, which may be either segmented or non-segmented, as well as other elements used to correct, protect, or enhance vision, including without limitation contact lenses, intra-ocular lenses, magnifying lenses and protective lenses or visors. Non-limiting examples of display elements and devices include screens and monitors. Non-limiting examples of windows include automotive, marine and aircraft windows, filters, shutters, and optical switches.

A preferred device for holding the composition of the invention in a mechanically stable can comprise a pair of opposed substrates having a gap there between for receiving the mixture of the host medium and said compound or said composition of the present invention, and a frame for holding said pair of substrates adjacent one another.

Another device of the present invention comprises an optical component provided with at least one transparent cell arrangement juxtaposed in a parallel direction to the surface thereof, as disclosed in WO 2006/013250, each cell being tightly closed and containing said fluid, mesomorphous or gel host medium and said at least one compound of the present invention. Other devices according to the invention can be a device as described in FR 2937154 or FR2950710 comprising at least one compound of the invention.

EXAMPLES

This invention will be further illustrated by the following non-limiting examples which are given for illustrative purposes only and should not restrict the scope of the appended claims.

Example 1

Synthesis of Compound 2-1: 1',1'''-[Naphthalene-1, 8-diyl-bis(methylene)]-bis{1-(2-isopropylphenyl)-[4,4'-bipyridine]-1,1'-diium}tetrakis(tetrafluoroborate)

A mixture of 1-(2,4-dinitrophenyl)-4,4'-bipyridinium chloride (15 g, 41.8 mmol) and 2-isopropylaniline (16.95 g, 125.5 mmol) in water (300 mL) was refluxed for 4 h, then cooled, filtered and the filtrate washed with CHCl$_3$ three times. The CHCl$_3$ extracts were discarded and the water was removed under reduced pressure. The residue was washed with acetone to give 1-(2-isopropylphenyl)-4,4'-bipyridinium chloride (9.17 g, 91%) as a yellow powder.

A solution of 1-(2-isopropylphenyl)-4,4'-bipyridinium chloride (5 g, 20.8 mmol) in water (40 mL) was added dropwise to NaBF$_4$ (6.8 g, 62 mmol) in water (40 mL). After stirring for 0.5 h the precipitate was filtered off and washed with the minimum of water to give 1-(2-Isopropylphenyl)-4,4'-bipyridinium tetrafluoroborate (5.25 g, 86%) as a pale yellow powder.

A mixture of 1,8-bis(bromomethyl)naphthalene (0.75 g, 2.4 mmol) and 1-(2-isopropylphenyl)-4,4'-bipyridinium tetrafluoroborate (2.59 g, 7.1 mmol) in MeCN (30 mL) was refluxed for 6 h. The mixture was cooled, filtered, washed with MeCN (3×10 mL) and air dried to give 1',1'''-[naphthalene-1,8-diyl-bis(methylene)]-bis{1-(2-isopropylphenyl)-[4,4'-bipyridine]-1,1'-diium}dibromide bis(tetrafluoroborate) (1.58 g, 64%) as brown needles.

1',1'''-[Naphthalene-1,8-diyl-bis(methylene)]-bis{1-(2-isopropylphenyl)-[4,4'-bipyridine]-1,1'-diium}dibromide bis(tetrafluoroborate) (1 g, 1 mmol) in hot water (15 mL) was added to NaBF$_4$ (1.06 g, 9.6 mmol) in water (30 mL). After stirring for 30 minutes the precipitate was filtered and washed with water to give, after drying, compound 2-1 (0.89 g, 88%) as a pale yellow powder.

$\delta_H$(400 MHz, CD$_3$OD-D$_2$O) 9.30 (4H, d, J=6.8 Hz), 9.19 (4H, d, J=6.8 Hz), 8.83 (4H, d, J=6.8 Hz), 8.79 (4H, d, J=6.8 Hz), 7.90-7.50 (10H, m), 7.26 (2H, d, J=7.2 Hz), 6.69 (4H, s), 2.58 (2H, sept, J=6.8 Hz), 1.27 (12H, d, J=6.8 Hz).

Example 2

Synthesis of Compound 2-2: 1',1'''-{[1,1'-Biphenyl]-2,2'-diylbis(methylene)}bis(1-(2-isopropylphenyl)-[4,4'-bipyridine]-1,1'-diium) tetrakis(tetrafluoroborate)

A solution of 1-(2-isopropylphenyl)-4,4'-bipyridinium tetrafluoroborate (3.19 g, 2.9 mmol), obtained according to example 1, and 2,2'-bis(bromomethyl)-1,1'-biphenyl (1 g, 2.9 mmol) in MeCN (40 mL) was refluxed for 60 h, cooled, filtered, washed with Et$_2$O (2×50 mL) and air dried. The resulting powder was dissolved in MeOH (20 mL) and added dropwise to a solution of NaBF$_4$ (3.88 g, 35 mmol) in water (50 mL) with stirring. The solvent was reduced and decanted. The residue was dissolved in hot water (30 mL), cooled, decanted and dried under vacuum to give the compound 2-2 (1.61 g, 51%) as a yellow powder.

$\delta_H$(400 MHz, D$_2$O) 9.15 (4H, d, J=6.8 Hz), 8.54 (4H, d, J=6.8 Hz), 8.49 (4H, d, J=6.8 Hz), 8.30 (4H, d, J=6.8 Hz), 7.76 (2H, d, J=7.6 Hz), 7.64 (4H, bs), 7.57 (2H, t, J=7.6 Hz), 7.41 (4H, bs), 7.28 (2H, t, J=7.2 Hz), 6.70 (2H, J=7.6 Hz), 5.82 (2H, d, J=15 Hz), 5.61 (2H, d, J=15 Hz), 2.41 (2H, sept, J=6.8 Hz), 1.09 (12H, d, J=6.8 Hz).

Example 3

Synthesis of Compound 1-1: 1,1'''-dihexyl-1,1''-[1,4-phenylenebis(methylene)]bis-4,4'-bipyridinium tetrakis(tetrafluoroborate)

A solution of 4,4'-bipyridine (40 g, 256 mmol) and 1-iodohexane (54.36 g, 256 mmol) in MeCN (200 mL) was heated at reflux. After 16 h the solvent was removed under reduced pressure and the residue dissolved in hot EtOH, cooled to 0° C. for 3 h and then filtered. The filtrate was crystallised from EtOH to give 1,1'-dihexyl-4,4-bipyridinium diiodide (14.6 g, 10%). The solvent was removed under reduced pressure and the residue dissolved in hot DCM and hexane (1 L) was added, the mixture filtered and the process repeated. The resulting precipitate was filtered through silica using MeOH (0-3% in DCM) as eluent. The first band was collected and the solvent removed under reduced pressure to give 1-hexyl-4,4'-bipyridinium iodide (57 g, 60%) as a pale yellow powder.

A solution of 1-hexyl-4,4'-bipyridinium iodide (3.68 g, 10 mmol) and 1,4-di(bromomethyl)benzene (1.06 g, 4 mmol) in MeCN (30 mL) was heated at reflux for 4 h in the dark, cooled, filtered and the residue washed with MeCN to give 1,1'''-dihexyl-1,1''-[1,4-phenylenebis(methylene)]bis-4,4'-bipyridinium dibromide diiodide (3.89 g, 82%) as an orange powder that was used directed in the next step.

A solution of 1,1'''-dihexyl-1,1''-[1,4-phenylenebis(methylene)]bis-4,4'-bipyridinium dibromide diiodide (1.5 g, 1.5 mmol) in MeOH (10 mL) was added dropwise to a solution of sodium tetrafluoroborate (1.04 g, 11.9 mmol) in water (20 mL) with stirring. The resulting mixture was stirred at room temperature for 10 min, filtered and the residue washed with water (10 mL) to give compound 1-1 (0.43 g, 31%) as a yellow powder.

$\delta_H$(400 MHz, DMSO-d$_6$) 9.47 (2H, d, J=6.8 Hz), 9.36 (2H, d, J=6.8 Hz), 8.77 (2H, d, J=6.8 Hz), 8.72 (2H, d, J=6.8 Hz), 7.70 (4H, s), 5.95 (4H, s), 4.69 (4H, t, J=7.6 Hz), 1.98 (4H, br.t), 1.32 (12H, br.s), 0.88 (6H, t, J=6.8 Hz).

Compounds 1-2 and 1-3 can be obtained by an analogous procedure using respectively 1,3-di(bromomethyl)- and 1,2-di(bromomethyl)-benzenes.

Example 4

Synthesis of Compound 2-3: 1',1'''-(Propane-1,3-diyl)bis{1-(2-isopropylphenyl)-[4,4'-bipyridine]-1,1'-diium}tetrakis(tetrafluoroborate)

A mixture of 1,3-diiodopropane (0.82 g, 2.8 mmol) and 1-(2-isopropylphenyl)-4,4'-bipyridinium tetrafluoroborate (2.5 g, 6.9 mmol) was refluxed in MeCN (30 mL). After 3 days the mixture was cooled, filtered and the residue washed with MeCN to give 1',1'''-(propane-1,3-diyl)bis{1-(2-isopropylphenyl)-[4,4'-bipyridine]-1,1'-diium}bis(tetrafluoroborate) diiodide (1.93 g, 68%) as a red powder.

1',1'''-(Propane-1,3-diyl)bis{1-(2-isopropylphenyl)-[4,4'-bipyridine]-1,1'-diium}bis(tetrafluoroborate) diiodide (1 g, 0.98 mmol) in water-MeOH (20 mL, 1:1) was added dropwise to a solution of NaBF$_4$ (0.94 g, 8.5 mmol) in water (50 mL) to give in the same manner described for Example 1, compound 2-3 (0.77 g, 84%) as an orange powder.

$\delta_H$(300 MHz, DMSO-d$_6$) 9.63 (4H, d, J=6.9 Hz), 9.42 (4H, d, J=6.9 Hz), 9.00-8.90 (8H, m), 7.80-7.50 (8H, m), 8.7.90-7.60 (8H, m), 4.87 (4H, t, J=7.2 Hz), 2.83 (2H, quin, J=7.2 Hz), 2.46 (2H, sept, J=6.6 Hz), 1.21 (12H, d, J=6.6 Hz).

Example 5

Synthesis of Compound 2-4: 1',1'''-(Propane-1,3-diyl)bis{1-(2-(trifluoromethoxy)phenyl)-[4,4'-bipyridine]-1,1'-diium}tetrakis(tetrafluoroborate)

A solution of 1-(2-(trifluoromethoxy)phenyl)-4,4'-bipyridinium tetrafluoroborate (5.13 g, 12.7 mmol) and 1,3-diiodopropane (1.48 g, 5 mmol) in MeCN (40 mL) was heated at reflux for 24 h then cooled and diluted with Et$_2$O (30 mL). The mixture was stirred for 5 min then left to stand for 0.5 h and filtered. The residue was crystallised from MeOH at 4° C. to give the mixed salt (2.18 g). This material was dissolved in MeOH—H$_2$O (10 ml, 1:1) and added dropwise to a solution of NaBF$_4$ (4.34 g, 39 mmol) in H$_2$O (30 mL) with stirring. Stirring was continued for 0.5 h. The mixture was filtered, washed with water (2×5 mL) and air dried to give compound 2-4 (1.51 g, 29%) as a yellow powder.

$\delta_H$ (300 MHz, DMSO-d$_6$) 9.31 (4H, d, J=7.0 Hz), 9.20 (4H, d, J=7.0 Hz), 8.72 (4H, d, J=7.0 Hz), 8.64 (4H, d, J=7.0 Hz), 7.90-7.60 (8H, m), 4.958 (4H, t, J=7.8 Hz), 2.92 (2H, quin, J=7.8 Hz).

$\delta_F$ (282 MHz, CD$_3$OD-D$_2$O) −59.10--−59.26 (bs), −152.40--−151.60 (bs).

Example 6

Synthesis of Compound 2-5: 1',1'''-(Propane-1,3-diyl)bis{1-(4-(trifluoromethoxy)phenyl)-[4,4'-bipyridine]-1,1'-diium}tetrakis(tetrafluoroborate)

A mixture of 1,3-diiodopropane (1.12 g, 3.8 mmol) and 1-[4-(trifluoromethoxy)phenyl]-4,4'-bipyridinium tetrafluoroborate (3.68 g, 9.1 mmol) in MeCN (20 mL) was heated under reflux. After 16 h the mixture was cooled, filtered and the residue air dried to give 1',1'''-(propane-1,3-diyl)bis{1-(4-(trifluoromethoxy)phenyl)-[4,4'-bipyridine]-1,1'-diium}diiodide bis(tetrafluoroborate) (0.89 g, 20%) as deep red needles.

A solution of 1',1'''-(propane-1,3-diyl)bis(1-(4-(trifluoromethoxy)phenyl)-[4,4'-bipyridine]-1,1'-diium) diiodide bis(tetrafluoroborate) (0.89 g, 0.75 mmol) in MeOH—H$_2$O (10 mL, 1:1) and added dropwise to a solution of NaBF$_4$ (1.64 g, 14.9 mmol) in H$_2$O (20 mL) with stirring. Stirring was continued for 0.5 h, the mixture filtered. The residue was dissolved in water-MeOH and the solvent was reduced in volume. The resulting precipitate was filtered, washed with cold MeOH (2 mL) and air dried to give 1',1'''-(propane-1,3-diyl)bis{1-(4-(trifluoromethoxy)phenyl)-[4,4'-bipyridine]-1,1'-diium}tetrakis (tetrafluoroborate) (0.32 g, 41%) as an orange powder.

$\delta_H$ (400 MHz, CD$_3$OD-D$_2$O) 9.45 (4H, d, J=7.1 Hz), 9.30 (4H, d, J=7.1 Hz), 8.80 (4H, d, J=7.1 Hz), 8.75 (4H, d, J=7.1 Hz), 8.03 (4H, d, J=8.4 Hz), 7.75 (4H, d, J=8.4 Hz), 5.03 (4H, t, J=7.8 Hz), 2.98 (2H, quin, J=7.8 Hz).

$\delta_F$ (376 MHz, CD$_3$OD-D$_2$O) −58.77 (s), −151.60--−151.80 (bs).

Example 7

Synthesis of Compound 2-6: 1',1'''-(2-Benzylpropane-1,3-diyl)bis(1-(2-isopropylphenyl)-[4,4'-bipyridine]-1,1'-diium) tetrakis(tetrafluoroborate)

Bromine (11.26 g, 70 mmol) was added dropwise to a suspension of NaBH$_4$ (6.08 g, 160 mmol) in 1,2-dimethoxyethane (70 mL) under N$_2$ with stirring at −20° C. After the addition the mixture was stirred at 0° C. for 2 h, cooled to −5° C. and diethyl 2-benzylmalonate (8 g, 32 mmol) was added. The mixture was allowed to warm to room temperature overnight, cautiously poured onto HCl (1 M, 100 mL) and EtOAc (100 mL) with rapid stirring at 5° C. The aqueous phase was separated and extracted with EtOAc (100 mL). The combined organic phases were washed with Na$_2$CO$_3$ (2×100 mL), water (100 mL), dried (Na$_2$SO$_4$) and the solvent removed under reduced pressure. The residue was filtered through silica using EtOAc (40-100% in hexanes) as eluent. The third band (R$_f$=0.05; 40% EtOAc in hexanes) was collected and the solvent removed under reduced pressure to give 2-Benzylpropane-1,3-diol (2.87 g, 54%) as a colourless oil which solidified on standing.

$\delta_H$ (400 MHz, CDCl$_3$) 7.10-7.4 (5H, m), 3.83 (2H, dd, J=4, 11 Hz), 3.69 (2H, dd, J=7, 11 Hz), 2.64 (2H, d, J=7 Hz), 2.35 (2H, bs), 2.02-2.16 (1H, m).

$\delta_C$ (100 MHz, CDCl$_3$) 139.85, 129.01, 128.48, 126.17, 65.64, 43.84.

Pyridine (1.57 g, 19.8 mmol) was added dropwise to a solution of triflic anhydride (5.60 g, 19.8 mmol) and 2-benzylpropane-1,3-diol (1.5 g, 9 mmol) in DCM (50 mL) at 0° C. with stirring. Stirring was continued for 1 h and the resulting mixture poured into water (100 mL), separated and the aqueous phase extracted with DCM (2×50 mL). The combined organic phases were dried (Na$_2$SO$_4$) and the solvent removed under reduced pressure. The residue was filtered through a short plug of silica using DCM as eluent and the solvent removed under reduced pressure to give the 2-Benzylpropane-1,3-diyl bis(trifluoromethanesulfonate) (3.35 g, 86%) as a colourless oil.

$\delta_H$ (400 MHz, CDCl$_3$) 7.10-7.50 (5H, m), 4.60 (2H, dd, J=4, 11 Hz), 4.50 (2H, dd, J=7, 11 Hz), 2.82 (2H, d, J=7 Hz), 2.55-2.70 (1H, m).

$\delta_F$ (376 MHz, CDCl$_3$) −74.25.

A solution of N-(2-isopropylphenyl)-4-(4-pyridyl)pyridinium tetrafluoroborate (2.79 g, 7.7 mmol) and 2-benzylpropane-1,3-diyl bis(trifluoromethanesulfonate) (1.50 g, 3.5 mmol) in MeCN (40 mL) was heated at reflux for 24 h, cooled and the solvent removed under reduced pressure. The residue was crystallised from hot EtOH, filtered, washed with EtOH and air dried to give the 1',1'''-(2-Benzylpropane-1,3-diyl)bis(1-(2-isopropylphenyl)-[4,4'-bipyridine]-1,1'-diium) bis(triflate) bis(tetrafluoroborate) (2.20 g, 55%) as a colourless powder.

$\delta_H$ (400 MHz, CD$_3$OD-D$_2$O) 9.30 (4H, d, J=7.2 Hz), 9.23 (4H, d, J=7.2 Hz), 8.74 (4H, d, J=7.2 Hz), 8.60 (4H, d, J=7.2 Hz), 7.74-8.87 (4H, m), 7.54-7.66 (4H, m) 7.15 (5H, br.s), 4.90-5.22 (4H, m), 3.67-3.80 (1H, m), 3.09 (2H, d, J=7.2 Hz), 2.52-2.66 (2H, m), 1.28 (12H, d, J=7.2 Hz).

$\delta_F$ (376 MHz, CD$_3$OD-D$_2$O) −79.65 (br.s) and −151.81--−151.92 (br.s).

A solution of 1',1'''-(2-benzylpropane-1,3-diyl)bis(1-(2-isopropylphenyl)-[4,4'-bipyridine]-1,1'-diium) bis(triflate) bis(tetrafluoroborate) (1.5 g, 1.3 mmol) in water-MeOH (10 mL, 1:1) was added dropwise to a solution of NaBF$_4$ (1.43 g, 13 mmol) in water (30 mL) with stirring. The mixture was heated to dissolution, cooled with rapid stirring, filtered and the residue crystallised from hot water, filtered, washed with water (2×5 mL) and air dried. The residue was again added to NaBF$_4$ (1.43 g, 13 mmol) in water (30 mL) and heated to dissolution, cooled, filtered, crystallised from hot water, filtered and air dried to give compound 2-6 (1.01 g, 75%) as a cream powder.

$\delta_H$ (400 MHz, CD$_3$OD-D$_2$O) 9.27 (4H, d, J=7.2 Hz), 9.20 (4H, d, J=7.2 Hz), 8.72 (4H, d, J=7.2 Hz), 8.57 (4H, d, J=7.2 Hz), 7.75-7.83 (4H, m), 7.55-7.63 (4H, m) 7.130 (5H, br.s), 4.94-5.19 (4H, m), 3.63-3.81 (1H, m), 3.08 (2H, d, J=7.2 Hz), 2.49-2.66 (2H, m), 1.26 (12H, d, J=7.2 Hz).

$\delta_F$ (376 MHz, CD$_3$OD-D$_2$O) −152.36--−152.46 (br.s).

Example 8

Synthesis of Compound 2-7: 1',1'''-[1,2-Phenylenebis(methylene)]bis{1-(2-isopropylphenyl)-[4,4'-bipyridine]-1,1'-diium}tetrakis(tetrafluoroborate)

A solution of 1-(2-isopropylphenyl)-4,4'-bipyridinium tetrafluoroborate (3.43 g, 9.5 mmol) and 1,2-bis(bromomethyl)benzene (1.00 g, 3.8 mmol) in MeCN (40 mL) was heated at reflux for 16 h. After cooling the mixture was filtered, washed with MeCN (2×5 mL) and air dried. The resulting hygroscopic yellow solid was dissolved in water (20 mL) and added dropwise to a solution of NaBF$_4$ (2.50 g, 22.7 mmol) in water (30 mL). The resulting mixture was heated to dissolution, cooled to room temperature with rapid stirring, filtered, washed with water (2×5 mL) and air dried to give compound 2-7 (1.40 g, 37%) as a colourless powder.

$\delta_H$ (400 MHz, CD$_3$OD-D$_2$O), 9.27 (4H, d, J=6.5 Hz), 9.20 (4H, d, J=6.5 Hz), 8.80 (4H, d, J=6.5 Hz), 8.76 (4H, d, J=6.5 Hz), 7.790 (4H, br.s), 7.65-7.75 (2H, m), 7.58 (4H, br.s), 7.40-7.50 (2H, m), 6.20 (4H, s), 2.57 (2H, m) and 1.25 (12H, d, J=6.8 Hz)

$\delta_F$, (376 MHz, CD$_3$OD-D$_2$O), −151.12--151.27 (br.s)

Example 9

Synthesis of Compound 2-8: 1',1'''-[1,2-Phenylenebis(methylene)]bis{1-(2-(trifluoromethoxy)phenyl)-[4,4'-bipyridine]-1,1'-diium}tetrakis(tetrafluoroborate)

A solution of 1-[2-(trifluoromethoxy)phenyl]-4,4'-bipyridinium tetrafluoroborate (3.83 g, 9.5 mmol) and 1,2-bis(bromomethyl)benzene (1.00 g, 3.8 mmol) in MeCN (40 mL) was heated at reflux for 16 h. After cooling, the mixture was filtered, washed with MeCN (2×5 mL) and air dried. The resulting yellow solid was dissolved in water (20 mL) and added dropwise to a solution of NaBF$_4$ (2.50 g, 22.7 mmol) in water (30 mL) with stirring. Stirring was continued for 0.5 h and the resulting precipitate filtered, washed with water (2×5 mL) and air dried to give compound 2-8 (1.73 g, 43%) as a colourless powder.

$\delta_H$ (400 MHz, CD$_3$OD-D$_2$O), 9.43 (4H, d, J=6.8 Hz), 9.23 (4H, d, J=6.8 Hz), 8.88 (4H, d, J=6.8 Hz), 8.79 (4H, d, J=6.8 Hz), 7.93-8.01 (4H, m), 7.82-7.88 (4H, t, J=7.6 Hz), 7.67-7.74 (2H, m), 7.40-7.48 (2H, m) and 6.23 (4H, s)

$\delta_F$, (376 MHz, CD$_3$OD-D$_2$O), −58.98 (s), 151.87--151.97 (br.s)

Example 10

Synthesis of Compound 1-4a: 1,3-Bis(1'-hexyl-4,4'-bipyridinium-1-yl)propane tetrakis(tetrafluoroborate)

A solution of 1-hexyl-4,4'-bipyridinium iodide (1.68 g, 4.6 mmol) and 1,3-diiodopropane (0.60 g, 0.45 mmol) in MeCN (50 mL) was heated at reflux for 4 days. The mixture was cooled, then filtered and the residue washed with DCM to give 1,3-Bis(1'-hexyl-4,4'-bipyridinium-1-yl)propane tetraiodide (1.29 g, 62%) as an orange powder.

A solution of 1,3-bis(1'-hexylbipyridinium-1-yl)propane tetraiodide (1.00 g, 0.97 mmol) in H$_2$O (50 mL) was added dropwise to a solution of sodium tetrafluoroborate (1.28 g, 11.6 mmol) in water (20 mL). The resulting mixture was stirred at room temperature for 10 min, filtered and washed with water (20 mL) to give compound 1-4a (0.21 g, 25%) as an orange powder.

$\delta_H$ (400 MHz, DMSO-d$_6$,) 9.50-9.30 (8H, m), 8.85 (4H, d, J=6.8 Hz), 8.79 (4H, d, J=6.8 Hz), 4.82 (4H, t, J=7.2 Hz), 4.70 (4H, t, J=7.2 Hz), 2.90-2.70 (2H, m), 2.10-1.90 (4H, m), 1.40-1.20 (12H, m), 0.88 (6H, t, J=6.8 Hz).

Compound 1-4b can be obtained through an identical procedure by substituting the counterion with ClO$_4^-$.

Example 11

Synthesis of Compound 1-5: 1,4-Bis(1'-hexyl-4,4'-bipyridinium-1-yl)butane tetrakis(tetrafluoroborate)

A solution of 1-hexylbipyridinium iodide (3.68 g, 10 mmol) and 1,4-diiodobutane (1.24 g, 4 mmol) in MeCN (80 mL) was heated at reflux for 2 weeks. The mixture was cooled, then filtered and the residue washed with MeCN to give 1,4-Bis(1'-hexyl-4,4'-bipyridinium-1-yl)butane tetraiodide (3.32 g, 79%) as an orange powder.

A solution of 1,4-bis(1'-hexyl-4,4'-bipyridinium-1-yl)butane tetraiodide (3 g, 2.9 mmol) in warm (50° C.) H$_2$O (10 mL) was added dropwise to a solution of sodium tetrafluoroborate (2.52 g, 23 mmol) in water (10 mL) at 0° C. with stirring. The resulting mixture was stirred at room temperature for 10 min. Water (150 mL) was added and heating was continued until dissolution was complete. The solution was cooled to 0° C., filtered, washed with water (2×10 mL) and filtered to give compound 1-5 (2.54 g, 63%) as an orange powder.

$\delta_H$ (400 MHz, DMSO-d$_6$,) 9.50-9.20 (8H, m), 8.90-8.70 (8H, m), 4.77 (4H, br.s), 4.70 (4H, t, J=7.6 Hz), 2.10 (4H, br.s), 1.99 (4H, br.s), 1.33 (12H, br.s), 1.00-0.80 (6H, m).

Example 12

Synthesis of Compound 2-9: 1',1'''-[1,2-Phenylenebis(methylene)]bis{1-(2-cyanophenyl)-[4,4'-bipyridine]-1,1'-diium}tetrakis(tetrafluoroborate)

A solution of 1-(2-cyanophenyl)-4,4'-bipyridinium tetrafluoroborate (2 g, 5.8 mmol) and 1,2-bis(bromomethyl)benzene (0.61 g, 2.3 mmol) in MeCN (40 mL) was heated at reflux for 16 h, cooled and filtered. The product was washed with MeCN (2×5 mL) and air dried. The resulting solid and NaBF$_4$ (2.64 g, 30 mmol) were heated in water (100 mL) and MeOH (100 mL) until dissolution, filtered through celite, cooled and the solvent reduced. The resulting precipitate was filtered, washed with water (2×30 mL) and air dried to give Compound 2-9 (1.41 g, 63%) as a cream powder.

$\delta_H$ (400 MHz, DMSO-d$_6$) 9.83 (4H, d, J=6.5 Hz), 9.47 (4H, d, J=6.5 Hz), 9.11 (4H, d, J=6.5 Hz), 9.00 (4H, d, J=6.5 Hz), 8.38 (2H, d, J=7.6 Hz), 8.10-8.25 (4H, m), 8.03 (2H, t, J=7.2 Hz), 7.50-7.65 (2H, m), 7.25-7.35 (2H, m), 6.24 (s, 4H).

$\delta_F$ (376 MHz, DMSO-d$_6$) −148.0--148.2 (br.s).

Example 13

Synthesis of Compound 2-10: 1',1'''-[Quinoxaline-2,3-diylbis(methylene)]bis{1-(2-cyanophenyl)-[4,4'-bipyridine]-1,1'-diium}tetrakis(tetrafluoroborate)

A solution of 1-(2-cyanophenyl)-4,4'-bipyridinium tetrafluoroborate (2.73 g, 7.9 mmol) and 2,3-bis(bromomethyl)quinoxaline (1.00 g, 3.2 mmol) in MeCN (40 mL) was heated at reflux for 16 h, and cooled. The product was filtered, washed with MeCN (2×5 mL) and air dried. The green solid in hot water (40 mL) and MeOH (40 mL) was added dropwise to NaBF$_4$ (4.18 g, 38 mmol) in water (40 mL) with stirring. The mixture was heated to dissolution, filtered through celite, cooled, then filtered, washed with water (2×10 mL) and air dried. The residue was crystallised from hot water-MeOH, filtered washed with MeOH (5 mL) and air dried to give Compound 2-10 (1.47 g, 48%) as a pale yellow powder.

$\delta_H$ (400 MHz, DMSO-d$_6$) 9.60 (4H, d, J=6.8 Hz), 9.44 (4H, d, J=6.8 Hz), 9.01 (4H, d, J=6.8 Hz), 8.93 (4H, d, J=6.5 Hz), 8.26 (2H, d, J=7.5 Hz), 8.00-8.20 (6H, m), 7.80-7.95 (4H, m) and 6.72 (4H, m).

$\delta_F$ (376 MHz, DMSO-d$_6$) −151.1--151.2 (br.s).

Example 14

Synthesis of Compound 2-11: 1',1'''-[Quinoxaline-2, 3-diylbis(methylene)]bis{1-(2-(trifluoromethoxy) phenyl)-[4,4'-bipyridine]-1,1'-diium}tetrakis(tetrafluoroborate)

A solution of 1-(2-trifluoromethoxyphenyl)-4,4'-bipyridinium tetrafluoroborate (3.07 g, 7.9 mmol) and 2,3-bis(bromomethyl)quinoxaline (1.00 g, 3.2 mmol) in MeCN (40 mL) was heated at reflux for 16 h then cooled. The product was filtered, washed with MeCN (2×5 mL) and air dried. The green solid in hot water (30 mL) and MeOH (20 mL) was added dropwise to $NaBF_4$ (4.18 g, 38 mmol) in water (30 mL) with stirring. Stirring was continued for 0.5 h and the resulting precipitate filtered and washed with water (2×10 mL). The residue was crystallised from hot water-MeOH, filtered and washed with MeOH (5 mL) and air dried to give Compound 2-11 (2.25 g, 67%) as lime green plates.

$\delta_H$ (400 MHz, DMSO-$d_6$) 9.81 (4H, d, J=6.5 Hz), 9.50 (4H, d, J=6.5 Hz), 9.15 (4H, d, J=6.5 Hz), 9.11 (4H, d, J=6.5 Hz), 8.13 (2H, d, J=7.7 Hz), 7.80-8.05 (10H, m) and 6.65 (4H, s).

$\delta_F$ (376 MHz, DMSO-$d_6$) −57.03 (s) and −148.1_−148.2 (br.s).

Example 15

Synthesis of Compound 2-12: 1',1'''-[Quinoxaline-2, 3-diylbis(methylene)]bis{1-(2-isopropylphenyl)-[4, 4'-bipyridine]-1,1'-diium}tetrakis(tetrafluoroborate)

A solution of 1-(2-isopropylphenyl)-4,4'-bipyridinium tetrafluoroborate (2.07 g, 7.9 mmol) and 2,3-bis(bromomethyl)quinoxaline (1.00 g, 3.2 mmol) in MeCN (40 mL) was heated at reflux for 16 h, cooled. The product was filtered, washed with MeCN (2×5 mL) and air dried. The yellow solid and $NaBF_4$ (4.18 g, 38 mmol) were heated to dissolution in water (20 mL) and MeOH (10 mL), and cooled. The product was filtered, washed with water (2×5 mL), acetone (4 mL) and air dried to give Compound 2-12 (1.28 g, 37%) as a pale yellow powder.

$\delta_H$ (400 MHz, DMSO-$d_6$) 9.69 (4H, d, J=6.5 Hz), 9.49 (4H, d, J=6.5 Hz), 9.00-9.20 (8H, m), 7.70-7.95 (10H, m), 7.55-7.65 (2H, m), 6.51 (4H, s), 2.48 (2H, m) and 1.24 (12H, t, J=7.2 Hz).

$\delta_F$ (376 MHz, DMSO-$d_6$) −148.1-148.2 (br.s).

Example 16

Synthesis of Compound 2-13: 1',1'''-[Pyridine-2,6-diylbis(methylene)]bis{1-(2-isopropylphenyl)-[4,4'-bipyridine]-1,1'-diium}tetrakis(tetrafluoroborate)
2,6-Bis(bromomethyl)pyridine Sodium borohydride (5 g, 131 mmol) was added portionwise to a solution of dimethyl pyridine-2,6-dicarboxylate (5.5 g, 28 mmol) in dry EtOH (85 mL) under $N_2$ at 0° C. with stirring. The resulting mixture was warmed to room temperature and stirred for 3 h and then heated at reflux for 10 h. After this time the mixture was cooled and the solvent removed under reduced pressure. Water (200 mL) was added and the resulting solution extracted with EtOAc (20×50 mL). After drying ($Na_2SO_4$) the extracts were filtered through silica, using EtOAc as eluent, and the solvent removed under reduced pressure. The residue was triturated with $Et_2O$ and air dried. The resulting colourless powder was dissolved in HBr (48% aqueous, 15 mL) and heated at reflux for 2 h, then cooled and neutralised with conc. aqueous NaOH at 0° C. The product was filtered, washed with water (2×10 mL) and air dried to give 2,6-bis(hydroxymethyl)pyridine (1.39 g, 19%) as a colourless powder.
Compound 2-13

A solution of 2,6-bis(bromomethyl)pyridine (0.70 g, 2.6 mmol) in MeCN (50 mL) was added dropwise to a refluxing solution of 1-(2-isopropylphenyl)-4,4'-bipyridinium tetrafluoroborate (5.74 g, 15.8 mmol) in MeCN (50 mL) over 2 h with stirring under $N_2$. Heating was continued for 2 h more and then the solution was cooled and slowly diluted with $Et_2O$ with stirring. The resulting precipitate was decanted off to leave a gummy residue. The residue was dissolved in MeCN and acetone was added. The resulting precipitate was filtered, washed with acetone and dried to give a bright yellow hygroscopic solid. The solid was dissolved in water (20 mL) and added dropwise to a solution of $NaBF_4$ (5.81 g, 52.8 mmol) in water (50 mL) with stirring. The resulting precipitate was heated to dissolution and then the solution was cooled with rapid stirring. The precipitate was filtered off, then dissolved in hot water (10 mL), and again cooled with rapid stirring, the precipitated product was filtered, washed with water (5 mL) and air dried to give compound 2-13 (0.80 g, 30%) as a colourless powder.

$\delta_H$ [400 MHz, $(CD_3)_2CO$]: 9.30-9.15 (8H, m), 8.79 (4H, d, J=6.8 Hz), 8.73 (4H, d, J=6.8 Hz), 8.13 (1H, t, J=8.0 Hz), 8.85-8.72 (6H, m), 8.64-8.52 (4H, d, J=8.0 Hz), 6.05 (4H, s), 2.60 (2H, 2×sept., J=6.8 Hz), 1.25 (12H, d, J=6.8 Hz)

$\delta_F$ (376 MHz, $(CD_3)_2CO$]: 151.75 (s) and 151.62 (t, J=1 Hz)

$\delta_{13C}$ [100.6 MHz, $(CD_3)_2CO$]: 152.19, 151.27, 150.71, 146.89, 146.46, 142.99, 140.49, 140.10, 132.53, 127.92, 127.69, 127.27, 127.11, 125.50, 124.11, 64.60, 27.74, 22.92.

Example 17

Synthesis of Compound 3-1: 1,1'-Bis-(3-tert-butylphenyl)-4,4'-bipyridinium bis(tetrafluoroborate)

A solution of 1,1'-bis-(2,4-dinitrophenyl)-4,4'-bipyridinium dichloride (3 g, 5.3 mmol) in hot water (50 mL) was added dropwise to a refluxing solution of 3-tert-butylaniline (4.78 g, 32 mmol) in water (50 mL). The resulting mixture was heated at reflux for 2 h, cooled, washed with $CHCl_3$ (3×50 mL) and the solvent removed under reduced pressure. The residue was dissolved in MeOH and acetone was added. The resulting precipitate was filtered and washed with acetone to give 1,1'-Bis-(3-tert-butylphenyl)-4,4'-bipyridinium dichloride (1.85 g, 70%) as a pale yellow powder that was used directly in the next stage.

A solution of 1,1'-bis-(3-tert-butylphenyl)-4,4'-bipyridinium dichloride (1.5 g, 3 mmol) in hot water-MeOH (20 mL) was added dropwise to a solution of sodium tetrafluoroborate (2.01 g, 18 mmol) in water (20 mL) at room temperature with stirring. The resulting mixture was stirred at room temperature for 10 min and filtered. The product was washed with water (10 mL), air dried and crystallized from hot MeOH. On cooling to 0° C. the precipitated product was filtered off and washed with MeOH to give Compound 3-1 (1.10 g, 61%) as a pale yellow powder.

$\delta_H$ (400 MHz, DMSO-$d_6$) 9.39 (4H, d, J=6.4 Hz), 8.79 (4H, d, J=6.4 Hz), 7.80-7.95 (4H, m), 7.57-7.75 (4H, m) and 1.39 (18H, s).

$\delta_F$ (376 MHz, DMSO-$d_6$) −155.4-−155.8 (bs).

Example 18

Synthesis of Compound 3-2: 1-(2-Trifluoromethoxyphenyl)-1'-(2-isopropylphenyl)-4,4'-bipyridinium bis(tetrafluoroborate)

A solution of 1-(2-isopropylphenyl)-4,4'-bipyridinium tetrafluoroborate (4 g, 11 mmol) and 2,4-dinitrophenyl p-toluenesulfonate (6.94 g, 20.5 mmol) in MeCN (40 mL) was heated at reflux for 2 days. The solvent was reduced, the residue was chilled to 0° C. and the resulting precipitate filtered, washed with cold MeCN (5 mL) and air dried to give 1-(2,4-dinitrophenyl)-1'-(2-isopropylphenyl)-4,4'-bipyridinium ditosylate (3.00 g, 35%). The solvent was removed and the residue dissolved in water —CHCl$_3$ (200 mL, 1:1), conc. HCl (0.8 mL) was added and the mixture filtered. The residue was dissolved in hot MeOH-water (80 mL, 1:1) and filtered into a solution of NaBF$_4$ (7.47 g, 68 mmol) in water (100 mL) with rapid stirring. After 0.5 h the resulting precipitate was filtered, washed with water (2×10 mL) and air dried to give 1-(2,4-Dinitrophenyl)-1'-(2-isopropylphenyl)-4,4'-bipyridinium bis(tetrafluoroborate) (2.72 g, 40%) as a pale yellow powder.

A solution of 1-(2,4-dinitrophenyl)-1'-(2-isopropylphenyl)-4,4'-bipyridinium bis(tetrafluoroborate) (1.44 g, 2.3 mmol) and 2-trifluoromethoxyaniline (0.83 g, 4.7 mmol) in MeOH (30 mL) was heated at reflux for 2 days. The mixture was cooled, poured into water (200 mL) and washed with CHCl$_3$ (3×100 ml) and the solvent removed under reduced pressure. The residue was triturated with EtOH to give Compound 3-2 (1.10 g, 77%) as a pale yellow powder.

$\delta_H$ (300 MHz, CD$_3$OD) 9.56 (2H, d, J=6.9 Hz), 9.42 (2H, d, J=6.9 Hz), 8.96 (2H, d, J=6.9 Hz), 8.91 (2H, d, J=6.9 Hz), 7.91-9.10 (2H, m), 7.73-7.89 (4H, m), 7.52-7.70 (2H, m), 2.64 (1H, m), 1.30 (6H, d, J=6.8 Hz).

$\delta_F$ (282 MHz, CD$_3$OD) −59.49 (s), −154.05-154.15 (br.s).

Example 19

Synthesis of Compound 3-3: 1-(2-Trifluoromethoxyphenyl)-1'-(4-trifluoromethoxyphenyl)-4,4'-bipyridinium bis(tetrafluoroborate)

A solution of 1-(2-trifluoromethoxyphenyl)-4,4'-bipyridinium tetrafluoroborate (2.30 g, 5.7 mmol) and 2,4-dinitrophenyl p-toluenesulfonate (2.87 g, 8.5 mmol) in MeCN (40 mL) was heated at reflux for 16 h. The solvent was removed under reduced pressure and the residue dissolved in water (200 mL), washed with CHCl$_3$ (3×50 mL). The solvent was removed under reduced pressure, the residue washed with EtOH and air dried to give 1-(2,4-Dinitrophenyl)-1'-(2-trifluoromethoxyphenyl)-4,4'-bipyridinium bis(tetrafluoroborate) (1.42 g, 38%) as a lime-coloured powder.

A solution of 1-(2,4-dinitrophenyl)-1'-(2-trifluoromethoxyphenyl)-4,4'-bipyridinium bis(tetrafluoroborate) (1.42 g, 2.2 mmol) and 4-trifluoromethoxyaniline (1.15 g, 6.5 mmol) in MeOH (20 mL) was heated at reflux for 2 h, cooled and the solvent removed under reduced pressure. The residue was twice triturated with hot EtOH. After cooling the product was filtered and air dried to give Compound 3-3 (1.04 g, 74%) as a cream powder.

$\delta_H$ (300 MHz, CD$_3$OD) 9.45-9.65 (4H, m), 8.80-9.03 (4H, m), 7.66-8.17 (8H, m).

$\delta_F$ (282 MHz, CD$_3$OD) −59.49 (s), −59.52 (s), −154.00-154.10 (br.s).

Example 20

Synthesis of Compound 3-4: 1,1'-Bis-(2-cyanophenyl)-4,4'-bipyridinium bis(tetrafluoroborate)

A solution of 1,1'-bis-(2,4-dinitrophenyl)-4,4'-bipyridinium dichloride (8 g, 14.3 mmol) in hot water (150 mL) was added dropwise to a refluxing solution of 2-aminobenzonitrile (10.1 g, 85.6 mmol) in water (150 mL). The resulting mixture was heated at reflux for 16 h, then cooled. The product was filtered, washed with CHCl$_3$ (3×100 mL) and the solvent removed under reduced pressure. The residue was washed with acetone to give 1,1'-Bis-(2-cyanophenyl)-4,4'-bipyridinium dichloride (5.96 g, 97%) as a tan powder.

A solution of 1,1'-bis-(2-cyanophenyl)-4,4'-bipyridinium dichloride (2 g, 4.6 mmol) in MeOH (20 mL) was added dropwise to a solution of sodium tetrafluoroborate (3.06 g, 27.8 mmol) in water (150 mL) with stirring. The resulting mixture was stirred at room temperature for 0.5 h, then filtered and washed with water (20 mL). Trituration with hot EtOH gave Compound 3-4 (1.99 g, 80%) as a tan powder.

$\delta_H$ (300 MHz, DMSO-d$_6$) 9.85 (4H, d, J=6.7 Hz), 9.22 (4H, d, J=6.7 Hz), 8.36 (2H, d, J=7.5 Hz), 8.10-8.25 (4H, m), 8.96-8.08 (2H, m).

$\delta_F$ (282 MHz, DMSO-d$_6$) −148.2-−148.4 (br.s).

Example 21

Synthesis of Compound 3-5: 1-(3-Cyanophenyl)-1'-(2-isopropylphenyl)-4,4'-bipyridinium bis(tetrafluoroborate)

A solution of 1-(2,4-dinitrophenyl)-1'-(2-isopropylphenyl)-4,4'-bipyridinium bis(tetrafluoroborate) (1.5 g, 2.4 mmol) and 3-aminobenzonitrile (0.57 g, 4.8 mmol) in MeOH-EtOH (40 mL, 1:1) was heated at reflux for 3 h, cooled and the solvent removed under reduced pressure. The residue was triturated with hot EtOH, cooled and filtered to give Compound 3-5 (1.25 g, 93%) as a pale yellow powder.

$\delta_H$ (300 MHz, CD$_3$OD) 9.52 (2H, d, J=6.9 Hz), 9.33 (2H, d, J=6.9 Hz), 8.84-8.97 (4H, m), 8.36-8.43 (1H, m), 8.17-8.32 (2H, m), 7.98-8.08 (1H, t, J=8 Hz), 7.74-7.84 (2H, m), 7.55-7.67 (2H, m), 2.61 (1H, m), 1.28 (6H, d, J=6.8 Hz).

$\delta_F$ (282 MHz, CD$_3$OD) −152.33-152.45 (br.s).

Example 22

Synthesis of Compound 3-6: 1-(2-tert-Butylphenyl)-1'-phenyl-4,4'-bipyridinium bis(tetrafluoroborate)

A solution of 1-(2,4-dinitrophenyl)-4,4'-bipyridinium chloride (5 g, 13.9 mmol) and 2-tert-butylaniline (6.23 g, 41.9 mmol) in water (150 mL) was heated at reflux for 7 days. After cooling, the mixture was filtered and washed with CHCl$_3$ (3×100 mL). The solvent was removed under reduced pressure and the residue washed with acetone to give 1-(2-tert-Butylphenyl)-4,4'-bipyridinium chloride (3.14 g, 69%) as a pale yellow powder.

A solution of 1-(2-tert-butylphenyl)-4,4'-bipyridinium chloride (3.1 g, 9.5 mmol) in water (30 mL) was added dropwise to a solution of NaBF$_4$ (3.15 g, 28.6 mmol) in water (30 mL) with stirring. The mixture was stirred for 0.5 h and filtered. The residue was washed with water (10 mL) and air dried to give 1-(2-tert-Butylphenyl)-4,4'-bipyridinium tetrafluoroborate (3.08 g, 86%) as a colourless powder.

A solution of 1-(2-tert-butylphenyl)-4,4'-bipyridinium tetrafluoroborate (2.61 g, 6.9 mmol) and 2,4-dinitrophenyl p-toluenesulfonate (3.52 g, 10.4 mmol) in MeCN (30 mL) was heated at reflux for 24 h. After cooling the mixture was filtered and washed with MeCN to give 1-(2,4-dinitrophenyl)-1'-(2-tert-butylphenyl)-4,4'-bipyridinium ditosylate (1.97 g, 35%). The solvent was removed under reduced pressure and the residue triturated with MeOH-Et$_2$O (1:1, 200 mL). After filtration, the solvent was removed under reduced pressure. The residue was subjected to Soxhlet extraction with Et$_2$O for 2 days. The residue from the extraction thimble was dissolved in hot MeOH-water (100 mL, 4:1) and filtered into a solution of NaBF$_4$ (17.5 g, 159 mmol) in water (300 mL) with rapid stirring. After 0.5 h the resulting precipitate was filtered, washed with water (2×20 mL). The residue was crystallised from hot MeOH-water (4:1, 100 mL) and air dried to give 1-(2-tert-Butylphenyl)-1'-(2,4-dinitrophenyl)-4,4'-bipyridinium bis(tetrafluoroborate) (2.17 g, 50%) as cream plates.

A solution of 1-(2-tert-butylphenyl)-1'-(2,4-dinitrophenyl)-4,4'-bipyridinium bis(tetrafluoroborate) (1.5 g, 2.4 mmol) and aniline (0.44 g, 4.7 mmol) in MeOH (30 mL) was refluxed for 2 h, cooled and the solvent removed under reduced pressure. The residue was triturated (twice) with hot EtOH (20 mL) and recrystallised (twice) from EtOH containing a few drops of water to give Compound 3-6 (0.56 g, 43%) as colourless prisms.

$\delta_H$ (300 MHz, CD$_3$OD-D$_2$O) 9.43-9.53 (4H, m), 8.85-8.92 (4H, m), 7.90-7.98 (3H, m), 7.82-7.88 (3H, m), 7.77 (1H, t, J=7.5 Hz), 7.58 (1H, t, J=7.9 Hz), 7.47 (1H, t, J=7.9 Hz) 1.26 (9H, s).

$\delta_F$ (282 MHz, CD$_3$OD-D$_2$O) −152.34-152.44 (br.s).

Example 23

Synthesis of Compound 3-7: 1,1'-Bis-(2-tert-butylphenyl)-4,4'-bipyridinium bis(tetrafluoroborate)

A solution of 1,1'-bis-(2,4-dinitrophenyl)-4,4'-bipyridinium dichloride (6 g, 10.7 mmol) in hot water (100 mL) was added dropwise to a refluxing solution of 2-tert-butylaniline (9.56 g, 64.2 mmol) in water (100 mL). The resulting mixture was heated at reflux for 20 days, cooled then washed with CHCl$_3$ (2×50 mL). The solvent was removed under reduced pressure, the residue was dissolved in MeOH and precipitated with EtOAc to give 1,1'-Bis-(2-tert-butylphenyl)-4,4'-bipyridinium dichloride (2.30 g, 44%) as a pale yellow powder.

A solution of 1,1'-bis-(2-tert-butylphenyl)-4,4'-bipyridinium dichloride (1.5 g, 3.2 mmol) in hot water (5 mL) was added dropwise to a solution of sodium tetrafluoroborate (2.11 g, 22.2 mmol) in water (5 mL) at room temperature with stirring. The resulting mixture was stirred for 10 min, filtered and washed with water (5 mL). The residue was crystallised from MeOH to give Compound 3-7 (1.08 g, 59%) as pale yellow microplates.

$\delta_H$ (400 MHz, DMSO-d$_6$) 9.56 (4H, d, J=6.9 Hz), 8.89 (4H, d, J=6.9 Hz), 7.94 (2H, dd, J=1.1, 8.2 Hz), 7.76 (2H, dd, J=1.1, 8.2 Hz), 7.42-7.62 (4H, m), 1.28 (18H, s).

Example 24

Synthesis of Compound 3-8: 1-(2-Cyanophenyl)-1'-(2-isopropylphenyl)-4,4'-bipyridinium bis(tetrafluoroborate)

A solution of 1-(2,4-dinitrophenyl)-1'-(2-isopropylphenyl)-4,4'-bipyridinium bis(tetrafluoroborate) (1.5 g, 2.4 mmol) and 2-aminobenzonitrile (5.7 g, 48 mmol) in isopropanol (40 mL) was heated at reflux for 2 days. After cooling the solvent removed under reduced pressure. The residue was triturated with hot EtOH, cooled and filtered to give Compound 3-8 (1.08 g, 81%) as a colourless powder.

$\delta_H$ (300 MHz, CD$_3$OD) 9.577 (2H, d, J=6.9 Hz), 9.33 (2H, d, J=6.9 Hz), 9.00 (2H, d, J=6.9 Hz), 8.91 (2H, d, J=6.9 Hz), 8.00-8.30 (4H, m), 7.72-7.88 (2H, m), 7.54-7.67 (2H, m), 2.61 (1H, m), 1.28 (6H, d, J=6.8 Hz).

$\delta_F$ (282 MHz, CD$_3$OD) −152.79-152.90 (br.s).

Example 25

Evaluation of Oxido-Reduction Potential and of the Absorption Spectrum of the Compounds of the Invention The oxido-reduction potentials of the compounds are measure by a method of cyclic voltammetry with 3 electrodes.

The 3 electrodes used are:
1 Platinum working electrode
1 Platinum auxiliary or counter electrode
1 Platinum reference electrode which is immersed into a solution consisting of 0.01M AgNO$_3$+0.1M TBAP (tetrabutylamonium perchlorate) in acetonitrile.

The potential values indicated are the first reduction potential for the compounds, with regards to the standard hydrogen reference electrode (SHE).

The analyzed solution comprises 0.01M of the compound to be analyzed and 1M of TBAP salt.

The scan rate of the potential is fixed to 100 mV/s.

The absorption spectra of the compounds are measured with a solution comprising 0.01M of the compound to be analyzed, 0.02M Phenothiazine (Phtz) or 10-Methylphenothiazine (Mephtz) and 1M of TBAP salt in propylene carbonate as solvent.

This solution is introduced into a quartz tank where at least one glass electrode coated with Indium Tin Oxide (ITO) is placed in order to colour the analyzed compound on this electrode. The absorption spectrum of the compound in the time domain is measured by a spectrophotometer.

The reducing agent (phenothiazine for all compounds except compounds 1-3, 2-1, 2-2, 2-5 to 2-12, 3-1 and 3-6 using 10-methylphenothiazine) colours on another glass electrode coated with Indium Tin Oxide (ITO).

The potential applied between both electrodes, for activating the compounds, is equal to the addition, in absolute value, of $E^1_{red}$ of the compound+$E^1_{ox}$ of phenothiazine (which is $E^1_{ox}$=0.36V) or methylphenothiazine (which is $E^1_{ox}$=0.45V).

The absorption spectrum is read after 3 min of activation, in particular the $\lambda_{max}$ value, which corresponds to the maximum absorption peak within the visible spectrum (between 400 and 800 nm).

The results for each of the synthesized compounds are indicated in Table 1 below. $E^1_{red}$ corresponds to the first reduction potential. The colour indicated in Table 1 is the visual colour perceived by emmetropic eyes under day light conditions. It should be noted that the $\lambda_{max}$ value just gives an approximate indication of the colour of a particular compound. However, as a consequence of the broad nature of the absorption bands, the whole absorption spectrum has to be taken into account in order to understand the final perceived colour of any one compound.

TABLE 1
| Compound | Molecule | $E^1_{red}$ (V) | $\lambda_{max}$ (nm) | Colour |
|---|---|---|---|---|
| 1-1 | 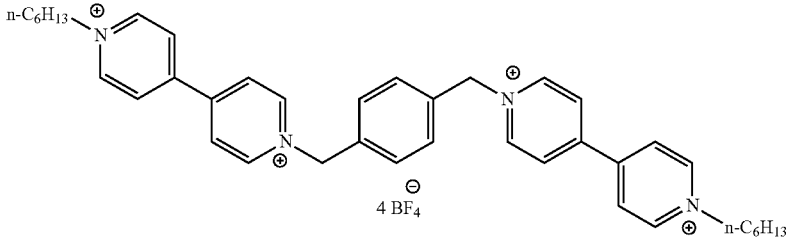 | / | / | blue |
| 1-2 | 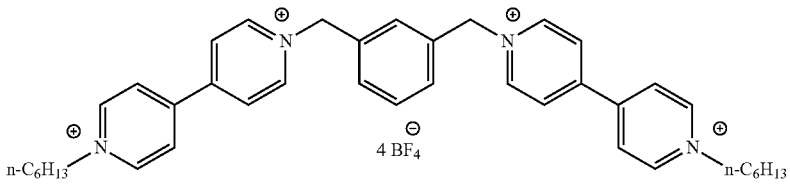 | / | / | blue |
| 1-3 | 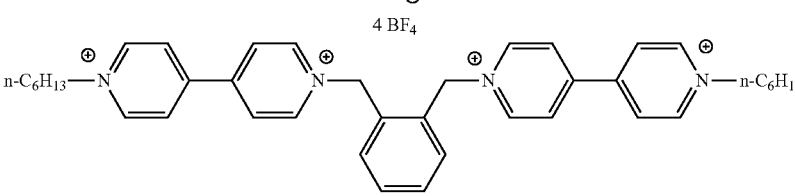 | −0.68 | 590 | purple |
| 1-4a | 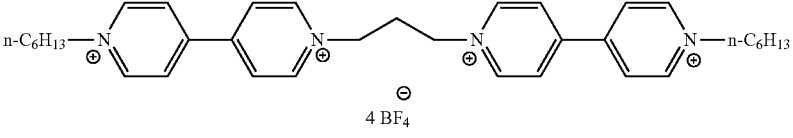 | −0.78 | / | purple |
| 1-4b | 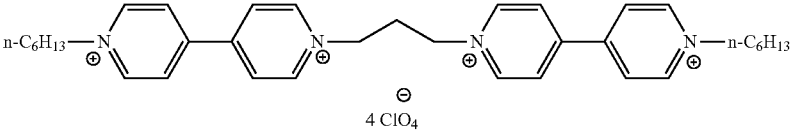 | / | / | purple |
| 1-5 | 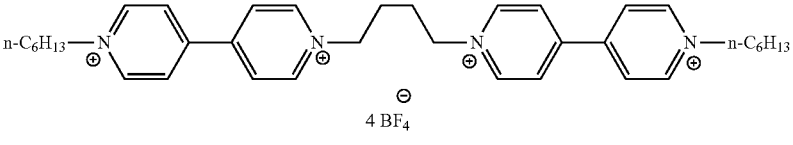 | / | / | blue |
| 2-1 | 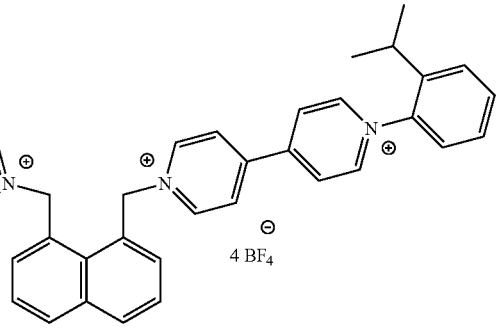 | −0.66 | 618 | blue |

TABLE 1-continued

| Compound | Molecule | $E^1_{red}$ (V) | $\lambda_{max}$ (nm) | Colour |
|---|---|---|---|---|
| 2-2 | [structure with 4 BF$_4^{\ominus}$] | −0.69 | 645 | Blue green |
| 2-3 | [structure with 4 BF$_4^{\ominus}$] | −0.73 | 607 | blue |
| 2-4 | [structure with OCF$_3$ groups, 4 BF$_4^{\ominus}$] | −0.64 | 597 | purple |
| 2-5 | [structure with F$_3$CO and OCF$_3$ groups, 4 BF$_4^{\ominus}$] | −0.58 | 597 | purple |
| 2-6 | [structure with Ph group, 4 BF$_4^{\ominus}$] | −0.66 | 594 | purple |
| 2-7 | [structure with 4 BF$_4^{\ominus}$] | −0.65 | 597 | purple |

TABLE 1-continued
| Compound | Molecule | $E^1_{red}$ (V) | $\lambda_{max}$ (nm) | Colour |
|---|---|---|---|---|
| 2-8 | 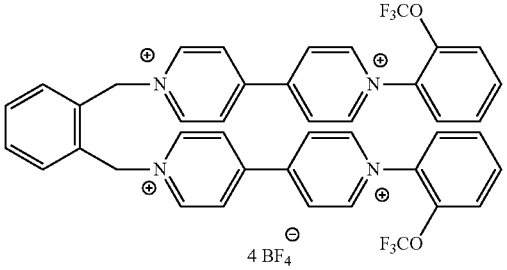 | −0.56 | 597 | purple |
| 2-9 | 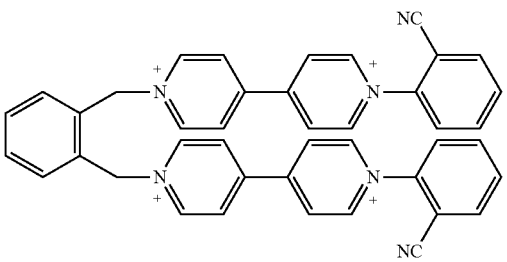 | −0.51 | 600 | Purple |
| 2-10 | 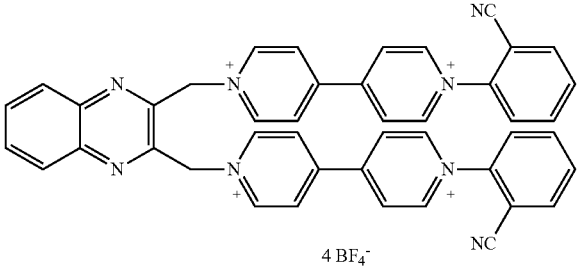 | −0.57 | 594 | Purple |
| 2-11 | 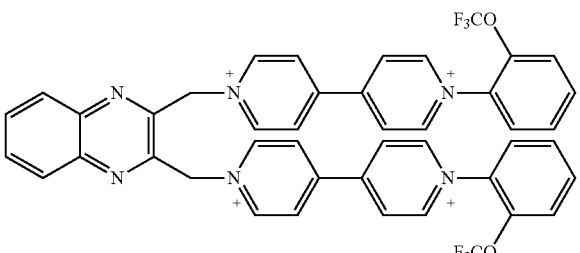 | −0.62 | 630 | blue |
| 2-12 | 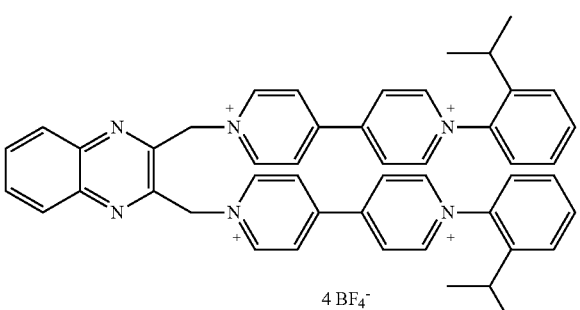 | −0.69 | 635 | blue |

TABLE 1-continued
| Compound | Molecule | $E^1_{red}$ (V) | $\lambda_{max}$ (nm) | Colour |
|---|---|---|---|---|
| 3-1 | 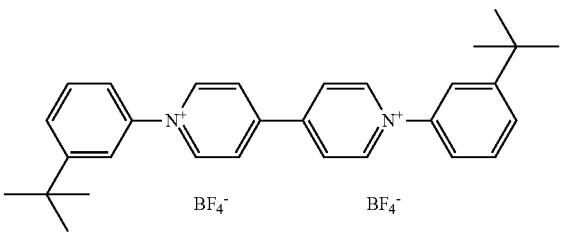 | −0.7 | 646 | green |
| 3-2 | 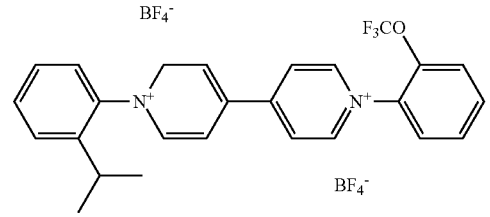 | −0.63 | 625 | Blue green |
| 3-3 | 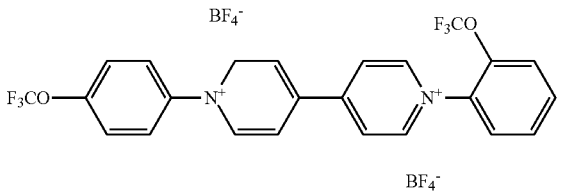 | −0.6 | 630 | green |
| 3-4 | 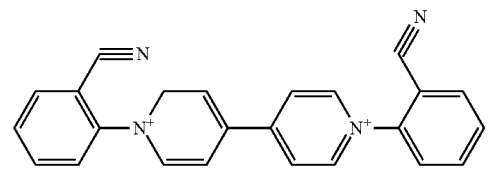 | −0.52 | 595 | Blue-green |
| 3-5 | 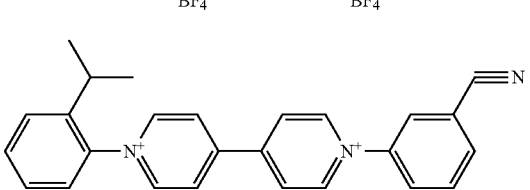 | −0.66 | 640 | green |
| 3-6 | 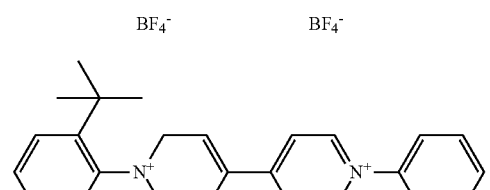 | −0.68 | 630 | green |
| 3-7 | 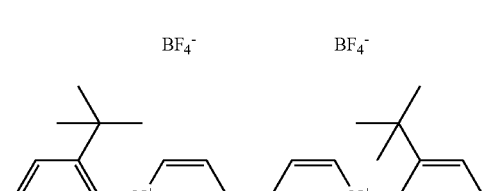 | −0.68 | 599 | blue |

TABLE 1-continued

| Compound | Molecule | $E^1_{red}$ (V) | $\lambda_{max}$ (nm) | Colour |
|---|---|---|---|---|
| 3-8 | 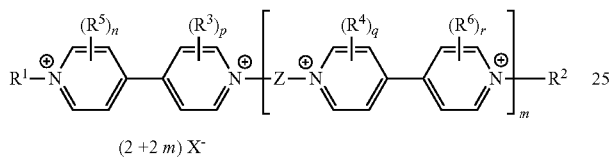 | −0.61 | 630 | Blue-green |

The invention claimed is:
1. A compound of formula (I):

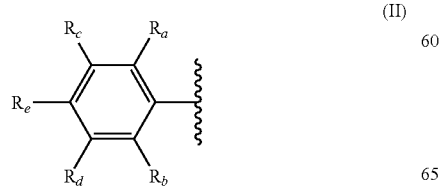

wherein:
Z is selected from:
  alkylene;
  cycloalkylene; and
  a bivalent groups of formula —R⁷—Y—R⁸—, wherein R⁷ and R⁸ are each independently selected from single bond, alkylene and cycloalkylene, and
  Y is selected from arylene, cycloalkylene, heteroarylene, arylene-arylene or arylene-CR'R''-arylene wherein R' and R'' form together with the carbon to which they are linked a carbocyclic group;
wherein said alkylene, cycloalkylene, arylene, heteroarylene and carbocyclic groups may be substituted by one or more substituents selected from halogen, alkyl, alkoxy, alkylthio, hydroxyalkyl, acyloxy, cycloalkyl, aryl, substituted aryl, aryloxy, heteroaryl and substituted heteroaryl;
wherein said alkylene, cycloalkylene, arylene, heteroarylene and carbocyclic groups may be substituted by one or more substituents selected from halogen, alkyl, alkoxy, alkylthio, hydroxyalkyl, acyloxy, cycloalkyl, aryl, substituted aryl, aryloxy, heteroaryl and substituted heteroaryl;
m is 0 or 1;
$R^1$ and $R^2$ are each independently selected from optionally substituted phenyl of formula (II):

(II)

wherein $R_a$, $R_b$, $R_c$, $R_d$ and $R_e$ are each independently selected from:
  H, halogen, cyano, nitro, alkyl, haloalkyl, haloalkoxy, (haloalkoxy)alkyl, arylalkyl, cycloalkyl, (cycloalkyl)alkyl and (heterocycloalkyl)alkyl, alkenyl, alkynyl, allyl, vinyl, aryl, substituted aryl, heteroaryl, substituted heteroaryl, —N(aryl)₂, —N(aryl)CO(aryl), —CO-aryl and —CO-substituted aryl;
  —OR⁹, —SR⁹, —S(O)R⁹, —S(O₂)R⁹, —S(O₂)NR⁹R¹⁰, —NR⁹R¹⁰, —NR⁹COR¹⁰, —NR⁹CO(aryl), —NR⁹aryl, —CH₂OR⁹, —CH₂SR⁹, —CH₂R⁹, —CO—R⁹ and —CO₂R¹⁰ wherein R⁹ and R¹⁰ are independently selected from H, alkyl, haloalkyl, arylalkyl, cycloalkyl, cycloalkylalkyl and heterocycloalkylalkyl;
  —S(O₂)NR¹¹R¹² and —NR¹¹R¹², wherein R¹¹ and R¹² form together with the nitrogen atom to which they are linked a saturated 5 to 7 membered heterocycloalkyl which may comprising in addition to the nitrogen atom one further heteroatom selected from oxygen, nitrogen and sulfur, and which may be optionally substituted by one or two groups, identical or different, selected from halogen, —R⁹, —OR⁹, and —NR⁹R¹⁰, wherein R⁹ and R¹⁰ are as defined above;
  —V—W—R¹³ wherein:
    V is selected from oxygen, —N(R⁹)—, sulfur, —S(O)— and —S(O₂)— wherein R⁹ is as defined above;
    W is alkylene, which may be substituted by a group selected from halogen and alkoxy; and
    R¹³ is selected from —OR⁹, —NR⁹(alkyl) and —SR⁹ wherein R⁹ is as defined above; and
  OC(O)—R¹⁴ wherein R¹⁴ is selected from alkyl, haloalkyl, alkenyl, —W—R¹³, and aryl group which may be substituted by 1 to 4 groups selected from halogen, —R⁹, —OR⁹, —SR⁹, —NR⁹R¹⁰, —NR¹¹R¹², —CO—R⁹, —CO₂R⁹ wherein R⁹, R¹⁰, R¹¹, R¹², R¹³ and W are as defined above,
with the provisions that:
  when Y is arylene-arylene or arylene-alkylene-arylene, then R¹ and R² are not phenyl;
  when m is 0, then $R_e$ is H and at least one of $R_a$, $R_b$ $R_c$ and $R_d$ is not H and may be independently selected from cyano, nitro, hydroxyl, C₄-C₁₂ alkyl, haloalkyl, alkoxy, haloalkoxy, alkoxycarbonyl, cycloalkyl, allyl, aryl and heteroaryl;
  R³, R⁴, R⁵ and R⁶ are each independently selected from H, alkyl, alkoxy, alkylthio, haloalkyl, haloalkoxy, haloalkylthio, polyalkylenoxy, alkoxycarbonyl, aryl, substituted aryl, heteroaryl and substituted heteroaryl, wherein the alkyl group may be substituted by one or more substituents selected from alkoxy, cycloalkyl, aryl, substituted aryl, heteroaryl and substituted heteroaryl;

n, p, q and r are each independently an integer from 0 to 4, wherein when n, p, q and r are two or more, each of the $R^3$, each of the $R^4$, each of the $R^5$ or each of the $R^6$ may be identical or different; and $X^-$ is a counterion.

2. The compound according to claim 1, wherein Z is selected from $C_1$-$C_{12}$ alkylene, aryl substituted $C_1$-$C_{12}$ alkylene, phenylene, naphthylene, ($C_1$-$C_4$ alkylene)-phenylene-($C_1$-$C_4$ alkylene), ($C_1$-$C_4$ alkylene)-naphthylene-($C_1$-$C_4$ alkylene), quinoxaline-2,3-diyl, ($C_1$-$C_4$ alkylene)-quinoxaline-2,3-diyl-($C_1$-$C_4$ alkylene), phenylene-phenylene, ($C_1$-$C_4$ alkylene)-phenylene-phenylene-($C_1$-$C_4$ alkylene) and phenylene-fluorenylene-phenylene, preferably Z is selected from —$CH_2$—, —$(CH_2)_2$—, —$(CH_2)_3$—, —$(CH_2)_4$—, —$(CH_2)_5$—, —$CH_2$—$CH(CH_3)$—$CH_2$—, —$CH_2$—$CH(CH_2Phenyl)$-$CH_2$—, —$(CH_2)_2$—$CH(CH_3)$—$CH_2$—, —$(CH_2)_3$—$CH(CH_3)$—$CH_2$—, —$(CH_2)_2$—$CH(CH_3)$—$(CH_2)_2$—,

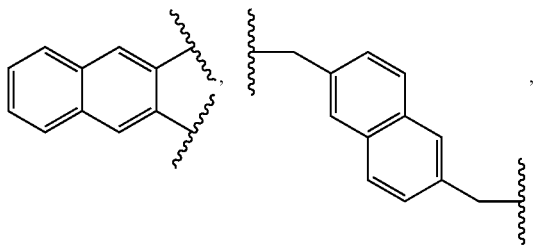

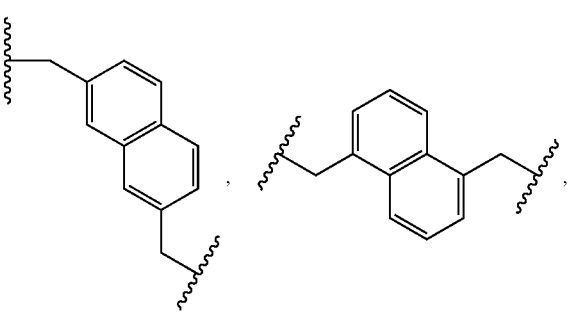

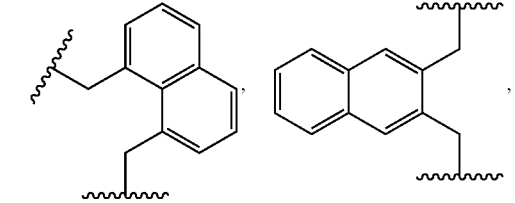

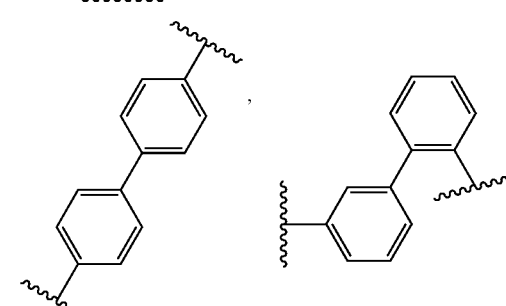

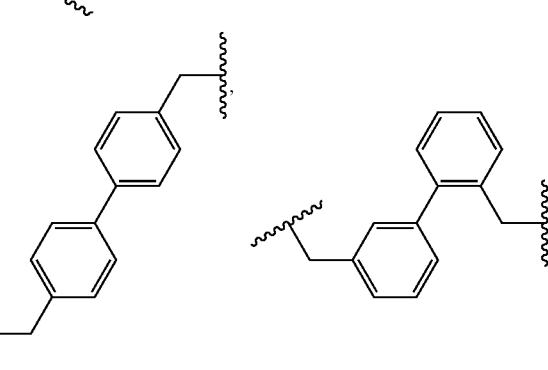

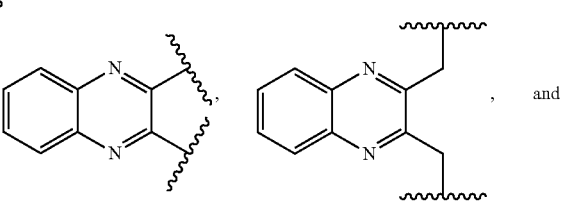

, and

-continued

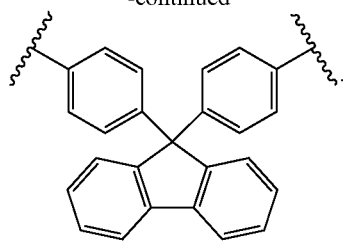

3. The compound according to claim 1, wherein $R^3$, $R^4$, $R^5$ and $R^6$ are each independently selected from $C_1$-$C_4$ alkyl, $C_1$-$C_4$ alkoxycarbonyl, alkanoyl, aroyl, aryl and heteroaryl, wherein the aryl and heteroaryl may be substituted by one or more substituents selected from $C_1$-$C_4$ alkyl and $C_1$-$C_4$ haloalkyl, preferably, $R^3$, $R^4$, $R^5$ and $R^6$ are each independently selected from methyl, ethoxycarbonyl, phenyl, p-methylphenyl and p-trifluoromethylphenyl.

4. The compound according to claim 1, wherein the counterion $X^-$ is selected from halide, tetrafluoroborate, tetraphenylborate, hexafluorophosphate, nitrate, methanesulfonate, trifluoromethane sulfonate, toluene sulfonate, hexachloroantimonate, bis(trifluoromethanesulfonyl)imide, perchlorate, acetate and sulfate.

5. The compound according to claim 1, wherein $R_a$, $R_b$, $R_c$, $R_d$ and $R_e$ are each independently selected from H, cyano, halogen, nitro, hydroxyl, alkyl, preferably $C_4$-$C_{12}$ alkyl, haloalkyl, alkoxy, haloalkoxy, alkoxycarbonyl, cycloalkyl, allyl, aryl and heteroaryl.

6. The compound according to claim 1, wherein $R_e$ is H and at least one of $R_a$, $R_b$, $R_c$, and $R_d$ is not H, preferably at least one of $R_a$ and $R_b$ is not H.

7. The compound according to claim 1, wherein said compound is selected from:

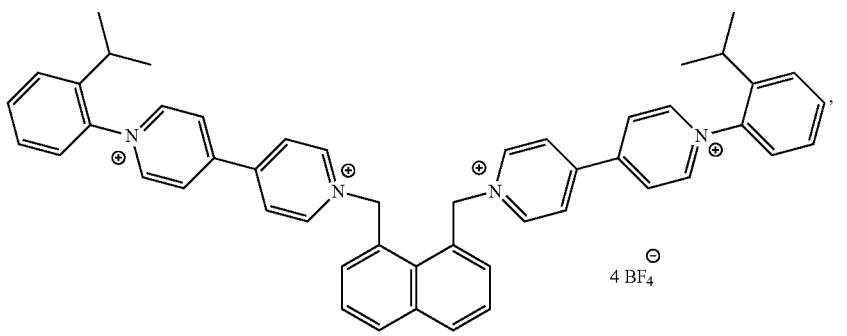

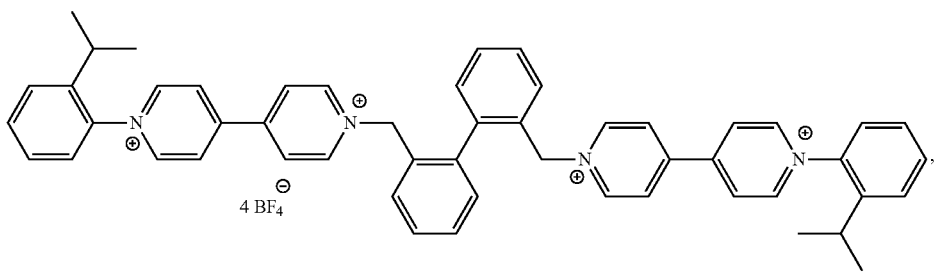

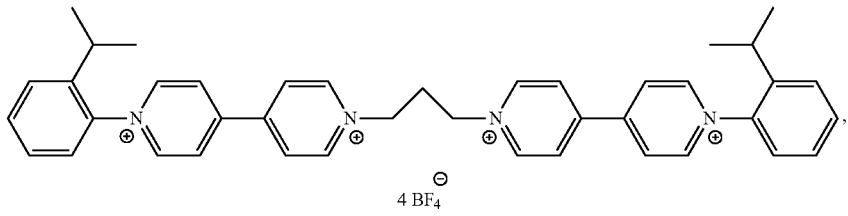

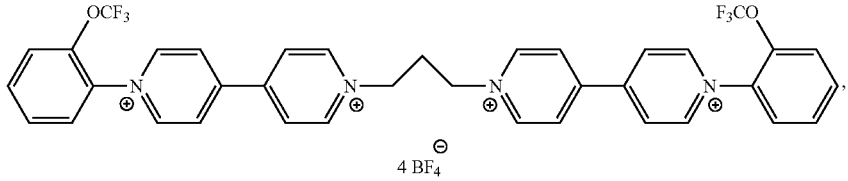

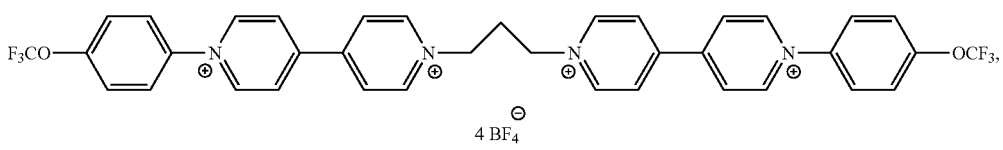

-continued
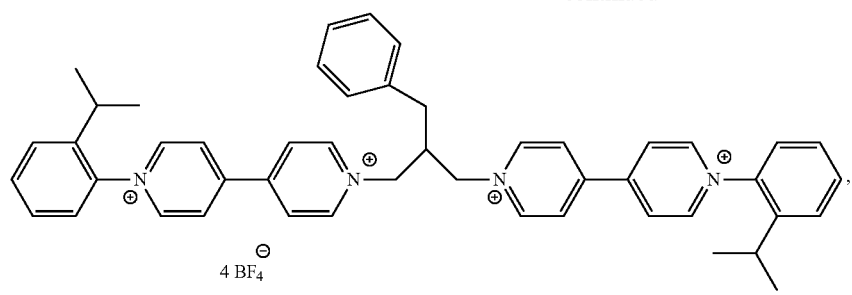
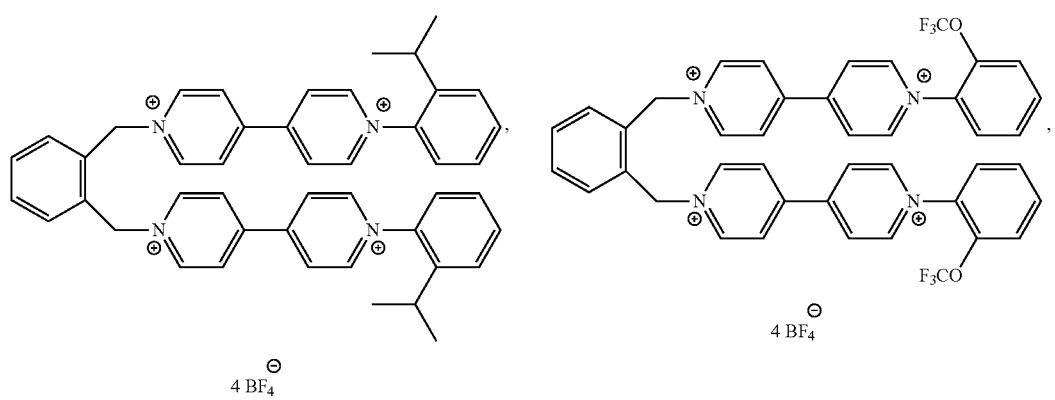
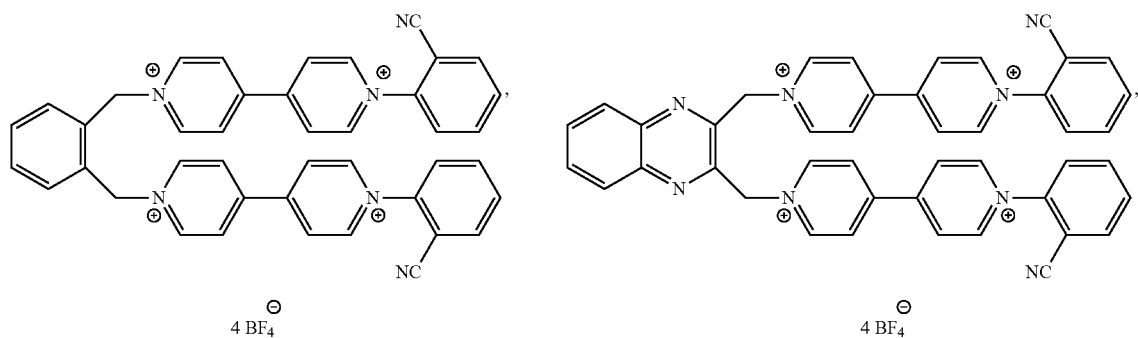
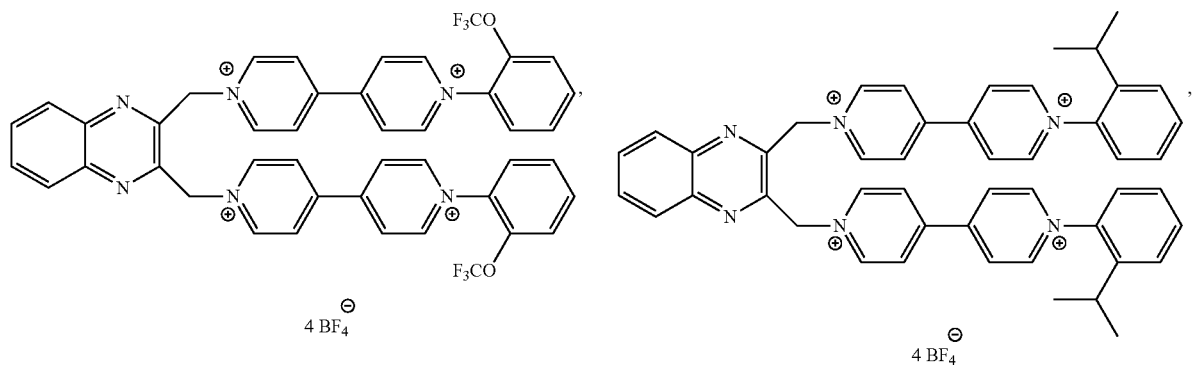

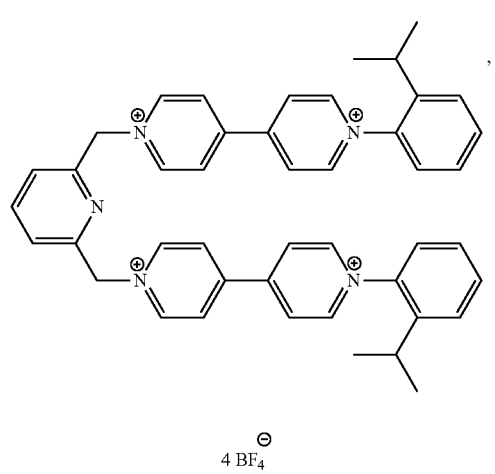

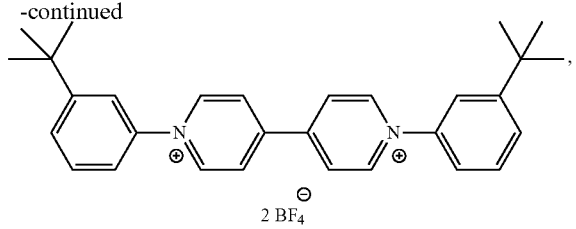

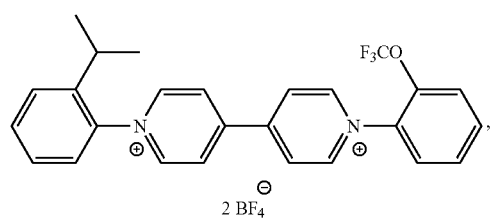

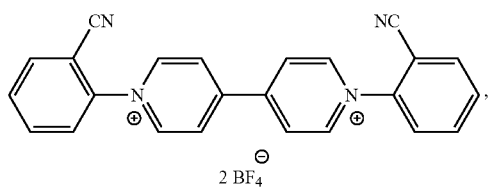

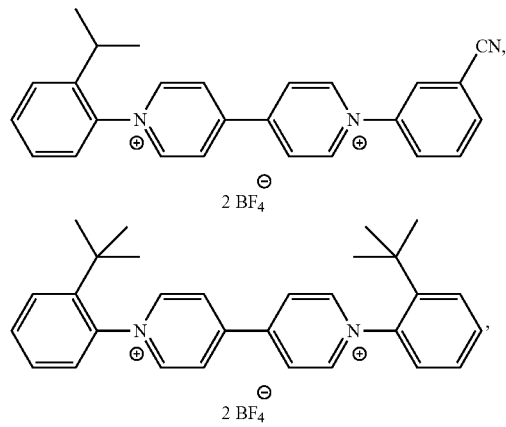

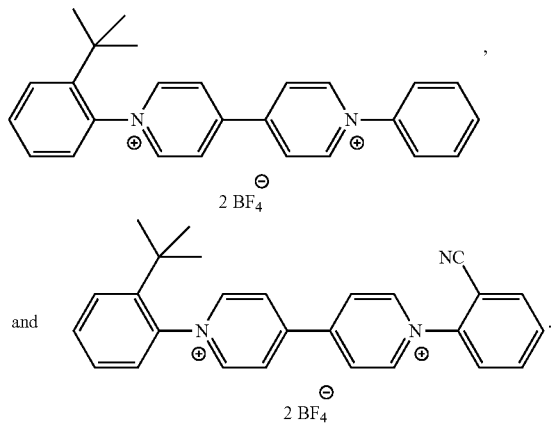

8. An electrochromic composition comprising at least one compound as defined in claim 1.

9. The electrochromic composition according to claim 8, wherein said composition comprises a fluid, mesomorphous or gel host medium.

10. The electrochromic composition according to claim 9, wherein the fluid or mesomorphous host medium is selected from the group consisting of organic solvents, liquid crystals, polymers, liquid crystal polymers and mixtures thereof.

11. An electrochromic device comprising a compound according to claim 1.

12. The electrochromic device according to claim 11, wherein said device comprises a mechanism for holding the said compound or said composition in a mechanically stable environment.

13. The electrochromic device according to claim 12, wherein said device comprises a pair of opposed substrates having a gap there between for receiving said compound or said composition, and a frame for holding said pair of substrates adjacent one another.

14. The electrochromic device according to claim 13, wherein said device comprises an optical component provided with at least one transparent cell arrangement juxtaposed in a parallel direction to the surface thereof, each cell being tightly closed and containing said compound or said composition.

15. The electrochromic device according to claim 11, wherein said electrochromic device is an optical article.

16. The electrochromic device according to claim 15, wherein the optical article is an optical lens or an optical filter, a window, a visor, a mirror or a display.

17. The electrochromic device according to claim 16, wherein the window is an aircraft window.

18. The electrochromic device according to claim 16, wherein the optical article is an optical lens.

19. The electrochromic device according to claim 16, wherein the opticle article is an ophthalmic lens.

20. A method for preparing the compound of formula (Ia)

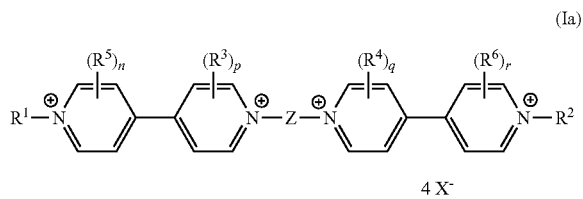

(Ia)

4 X⁻ wherein Z, $R^3$, $R^4$, $R^5$, $R^6$, n, p, q, r and $X^-$ are as defined in formula (I) and $R^1$ and $R^2$ are independently selected from optionally substituted phenyl groups of formula (II) wherein $R_a$, $R_b$, $R_c$, $R_d$ and $R_e$ are each independently selected from:
- H, halogen, cyano, nitro, alkyl, haloalkyl, haloalkoxy, (haloalkoxy)alkyl, arylalkyl, cycloalkyl, (cycloalkyl)alkyl and (heterocycloalkyl)alkyl, alkenyl, alkynyl, allyl, vinyl, aryl, substituted aryl, heteroaryl, substituted heteroaryl, —N(aryl)₂, —N(aryl)CO(aryl), —CO-aryl and —CO-substituted aryl;
- —$OR^9$, —$SR^9$, —$S(O)R^9$, —$S(O_2)R^9$, —$S(O_2)NR^9R^{10}$, —$NR^9R^{10}$, —$NR^9COR^{10}$, —$NR^9CO(aryl)$, —$NR^9aryl$, —$CH_2OR^9$, —$CH_2SR^9$, —$CH_2R^9$, —$CO$—$R^9$ and —$CO_2R^{10}$ wherein $R^9$ and $R^{10}$ are independently selected from H, alkyl, haloalkyl, arylalkyl, cycloalkyl, cycloalkylalkyl and heterocycloalkylalkyl;
- —$S(O_2)NR^{11}R^{12}$ and —$NR^{11}R^{12}$, wherein $R^{11}$ and $R^{12}$ form together with the nitrogen atom to which they are linked a saturated 5 to 7 membered heterocycloalkyl which may comprising in addition to the nitrogen atom one further heteroatom selected from oxygen, nitrogen and sulfur, and which may be optionally substituted by one or two groups, identical or different, selected from halogen, —$R^9$, —$OR^9$, and —$NR^9R^{10}$, wherein $R^9$ and $R^{10}$ are as defined above;
- —V—W—$R^{13}$ wherein:
  V is selected from oxygen, —$N(R^9)$—, sulfur, —$S(O)$— and —$S(O_2)$— wherein $R^9$ is as defined above;
  W is alkylene, which may be substituted by a group selected from halogen and alkoxy; and
  $R^{13}$ is selected from —$OR^9$, —$NR^9(alkyl)$ and —$SR^9$ wherein $R^9$ is as defined above; and
  OC(O)—$R^{14}$ wherein $R^{14}$ is selected from alkyl, haloalkyl, alkenyl, —W—$R^{13}$, and aryl group which may be substituted by 1 to 4 groups selected from halogen, —$R^9$, —$OR^9$, —$SR^9$, —$NR^9R^{10}$, —$NR_{11}R^{12}$, —CO—$R^9$, —$CO_2R^9$ wherein $R^9$, $R^{10}$, $R^{11}$, $R^{12}$, $R^{13}$ and W are as defined above;

comprising:
  the step (i) of alkylation of two bipyridinium salts (1) or (1'), with a bifunctional alkylating agent $ZL_2$ in which the leaving group is selected from sulfonate and carboxylate; and
  the step (ii) of an anion exchange with an aqueous solution of the desired counterion $X^-$

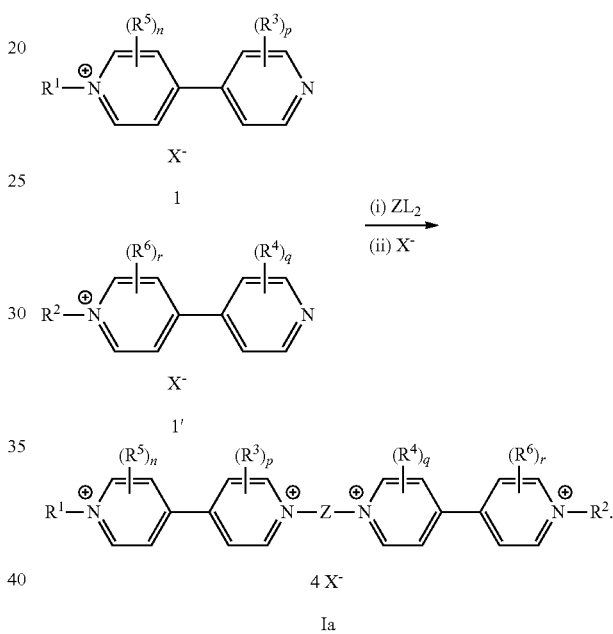

21. An electrochromic device comprising a composition according to claim 8.

* * * * *

UNITED STATES PATENT AND TRADEMARK OFFICE
CERTIFICATE OF CORRECTION

PATENT NO. : 9,823,534 B2
APPLICATION NO. : 15/022784
DATED : November 21, 2017
INVENTOR(S) : Stuart Aiken et al.

It is certified that error appears in the above-identified patent and that said Letters Patent is hereby corrected as shown below:

In the Claims

Claim 7, Column 52, Line 50:

Delete " 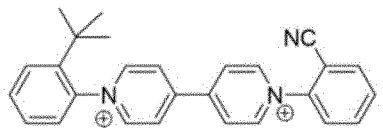  " and replace with -- 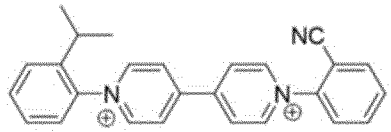  --.

Claim 12, Column 51, Line 64:
Delete "or said composition".

Signed and Sealed this
Ninth Day of October, 2018

Andrei Iancu
*Director of the United States Patent and Trademark Office*